US012630815B2

(12) United States Patent (10) Patent No.: US 12,630,815 B2

Iwata et al. (45) Date of Patent: May 19, 2026

(54) ARTIFICIAL GENE AND METHOD FOR MUTATING GENE

(71) Applicants: NATIONAL INSTITUTE OF ADVANCED INDUSTRIAL SCIENCE AND TECHNOLOGY, Tokyo (JP); UNIVERSITY OF TSUKUBA, Ibaraki (JP)

(72) Inventors: Yasushi Iwata, Tsukuba (JP); Kanako Tomita, Tsukuba (JP); Iwane Suzuki, Tsukuba (JP); Ryo Morioka, Tsukuba (JP); Tianjing Yang, Tsukuba (JP)

(73) Assignees: NATIONAL INSTITUTE OF ADVANCED INDUSTRIAL SCIENCE AND TECHNOLOGY, Tokyo (JP); UNIVERSITY OF TSUKUBA, Ibaraki (JP)

( * ) Notice: Subject to any disclaimer, the term of this patent is extended or adjusted under 35 U.S.C. 154(b) by 125 days.

(21) Appl. No.: 17/633,821

(22) PCT Filed: Aug. 7, 2020

(86) PCT No.: PCT/JP2020/030476

§ 371 (c)(1),
(2) Date: Feb. 8, 2022

(87) PCT Pub. No.: WO2021/029391

PCT Pub. Date: Feb. 18, 2021

(65) Prior Publication Data

US 2022/0298499 A1 Sep. 22, 2022

(30) Foreign Application Priority Data

Aug. 9, 2019 (JP) ................................. 2019-147468

(51) Int. Cl.
*C12N 15/01* (2006.01)
*A01H 1/06* (2006.01)

(52) U.S. Cl.
CPC .............. *C12N 15/01* (2013.01); *A01H 1/06* (2013.01)

(58) Field of Classification Search
None
See application file for complete search history.

(56) References Cited

U.S. PATENT DOCUMENTS

| | | | |
|---|---|---|---|
| 6,140,466 A | 10/2000 | Barbas, III et al. | |
| 6,258,567 B1 | 7/2001 | Chen et al. | |
| 2015/0284783 A1 | 10/2015 | Canton | |
| 2016/0367205 A1* | 12/2016 | Galbiati | ................... G01T 1/204 |

FOREIGN PATENT DOCUMENTS

| | | |
|---|---|---|
| JP | 2002-502249 A | 1/2002 |
| JP | 2018-000129 A | 1/2018 |
| JP | 2025-120223 A | 8/2025 |

OTHER PUBLICATIONS

Nelissen et al., Stable isotope labeling methods for DNA. Progress in Nuclear Magnetic Resonance Spectroscopy (2016), 96: 89-108 (Year: 2016).*
Poenitz et al., Study of the 15N (p, n) 150 reaction as a monoenergetic neutron source for the measurement of differential scattering cross sections. J. Instrumentation (2017), 12, p. 03016 (Year: 2017).*
Hill et al., Neutron carcinogenesis: past, present, and future. J. Radiat. Res. (1999), 40: Suppl, 117-127 (Year: 1999).*
Matsumoto et al., A rapid analysis for 15N-tracers by a proton reaction. Nuclear Instruments and Methods (1982), 196: 565-567 (Year: 1982).*
Dmitriev et al., Radiosensitivity of the slime mould Physarum polycephalum to gamma irradiation. Environmental and Experimental Botany (1980), 20: 247-250 (Year: 1980).*
Brewer, Repair of Radiation-Induced DNA Double-Strand Breaks in Isolated Nuclei of Physarum polycephalum. Radiation Research (1979), 79: 368-376 (Year: 1979).*
International Preliminary Report on Patentability (Chapter I) and Written Opinion of the International Searching Authority issued in PCT/JP2020/030476; issued Feb. 8, 2022.
Brigitte Rene et al., "General method of preparation of uniformly 13C, 15N-labeled DNA fragments for NMR analysis of DNA structures", Journal of Biomolecular NMR, vol. 36, No. 3, Oct. 4, 2006, pp. 137-146, Kluwer Academic Publishers.
Jamin N. et al., "NMR studies of protein-DNA interactions", Progress in Nuclear Magnetic Resonance Spectroscopy, vol. 38, No. 1, Jan. 15, 2001, pp. 83-114, Pergamon Press, GB.
Zimmer D. P. et al., "NMR of enzymatically synthesized uniformly 13C15N-labeled DNA oligonucleotides", Proceedings of the National Academy of Sciences, vol. 92, Apr. 1, 1995, pp. 3091-3095, National Academy of Sciences, USA.
Rangadurai Atul et al., "Characterizing micro-to-millisecond chemical exchange in nucleic acids using off-resonance R1p relaxation dispersion", Progress in Nuclear Magnetic Resonance Spectroscopy, vol. 112-113, May 11, 2019, pp. 55-102, Pergamon Press, GB.
International Search Report issued in PCT/JP2020/030476; mailed Oct. 20, 2020.
John M. Louis et al. "Preparation of Uniformly Isotope-Labeled DNA Oligonucleotides for NMR Spectroscopy" The Journal of Biological Chemistry, 1998, pp. 2374-2378, vol. 273, No. 4.

(Continued)

*Primary Examiner* — Catherine Konopka

(74) *Attorney, Agent, or Firm* — Studebaker Brackett PLLC

(57) ABSTRACT

An artificial gene has a $^{15}N$ abundance exceeding a natural abundance in bases of at least a portion of DNA. A method for mutating a gene includes a first step of producing a state in which $^{15}N$ is unevenly distributed into a prescribed DNA in a living cell; and a second step of irradiation with a proton beam at an energy at which the $^{15}N$ produces a resonant nuclear reaction.

13 Claims, 16 Drawing Sheets

Specification includes a Sequence Listing.

(56)            References Cited

OTHER PUBLICATIONS

James L. Baber et al. "Chemical Shift Mapped DNA-Binding Sites and 15N Relaxation Analysis of the C-Terminal KH Domain of Heterogeneous Nucleur Ribonucleoprotein K" Biochemistry, 2000, pp. 6022-6032, vol. 39, DOI:10.1021/bi000105e.

M. Michael Gromiha "Influence of DNA Stiffness in Protein-DNA Recognition" Journal of Biotechnology, 2005, pp. 137-145, vol. 117, DOI:10.1016/j.jbiotec.2004.12.016.

\* cited by examiner

Figure 4:
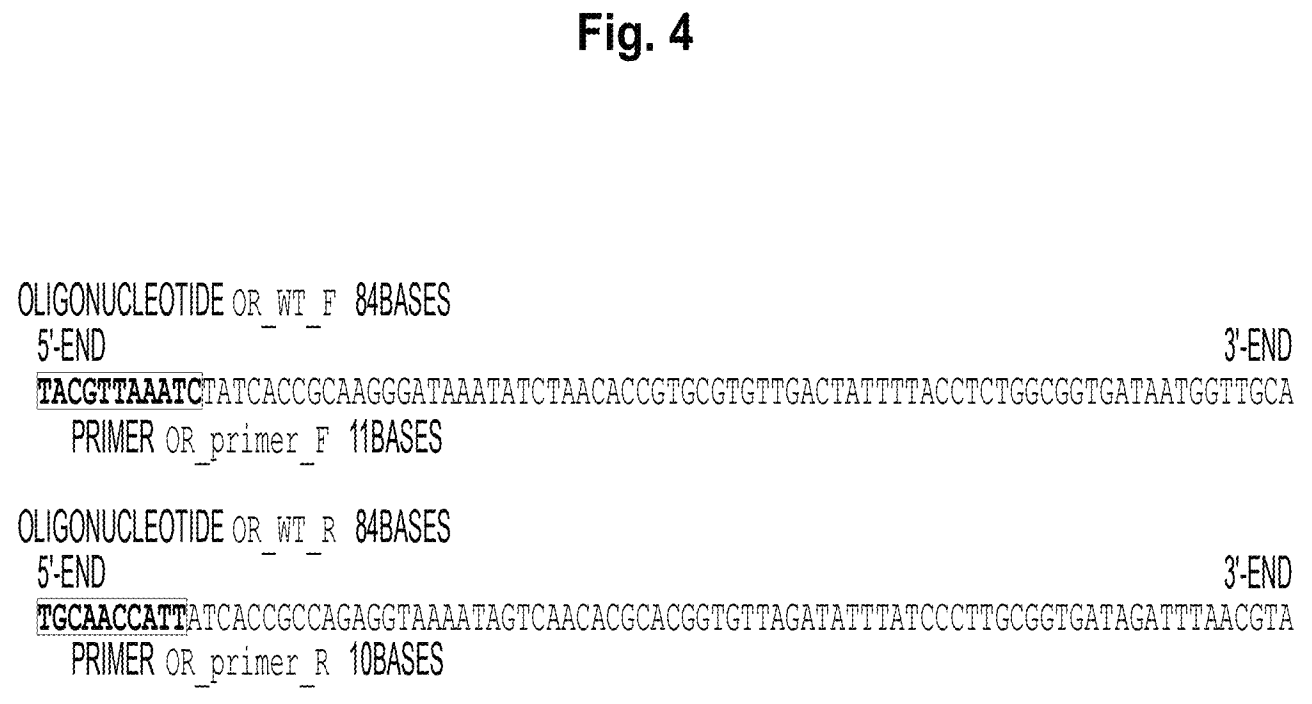

OLIGONUCLEOTIDE OR WT_F 84BASES

5'-END    3'-END
TACGTTAAATCTATCACCGCAAGGCATAAATATCTAACACCGTGCGTGTTGACTATTTACCTCTGGCGGGTGATAATGGTTGCA

PRIMER OR_primer_F 11BASES

OLIGONUCLEOTIDE OR WT_R 84BASES

5'-END    3'-END
TGCAACCATTATCACCGCCAGAGGTAAAATAGTCAACACGCACGGTGTTAGATATTTATCCCTTGCGGTGATAGATTTAACGTA

PRIMER OR_primer_R 10BASES

Fig. 11

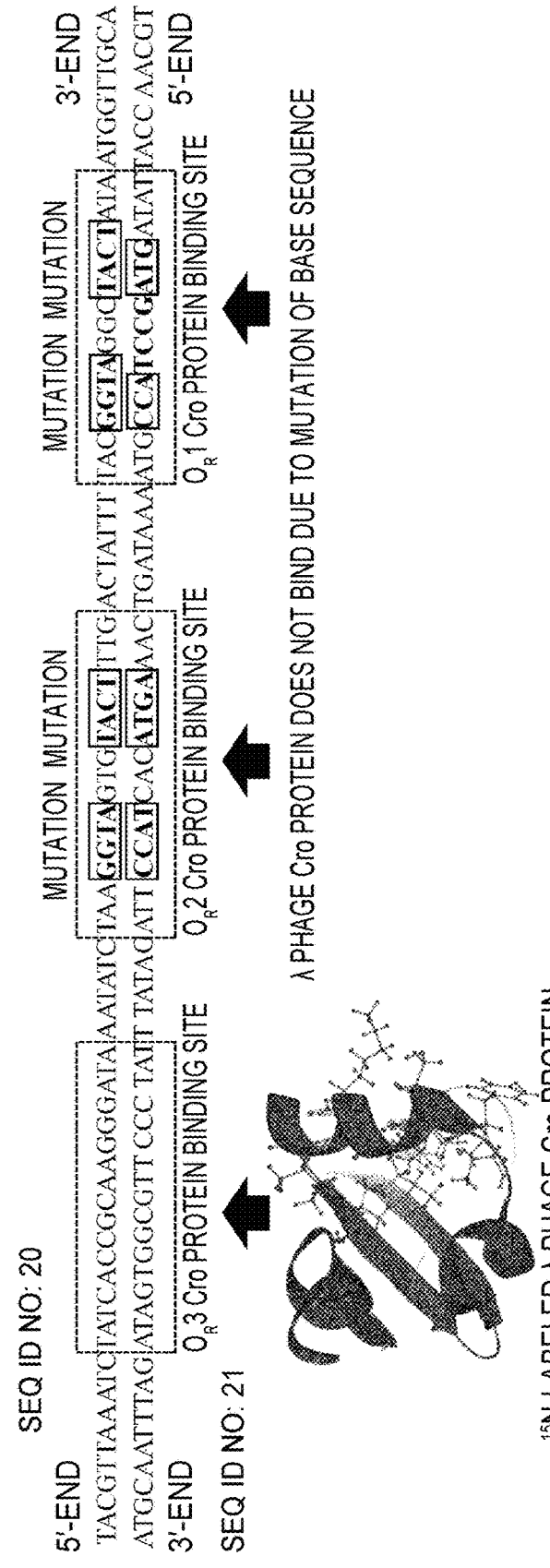

DNA BINDING SITE FOR λ PHAGE Cro PROTEIN

E. coli INFECTED WITH λ PHAGE

SEQ ID NO: 20

5'-END
TACGTTAAATCTATCACCGCAAGGGATAAAATATCTTAAGGTAGTGTAGTAGGCTAGGCTAGGCTATA ATGGTTGCA
ATGCAATTTAGATAGTGGCGTT CCC TATT TATACATT CCATCACATGAAACTGATAAAATGCCATCCGATATTACC AACGT
3'-END

O$_R$3 Cro PROTEIN BINDING SITE    O$_R$2 Cro PROTEIN BINDING SITE    O$_R$1 Cro PROTEIN BINDING SITE

SEQ ID NO: 21

MUTATION MUTATION    MUTATION MUTATION    3'-END
5'-END

λ PHAGE Cro PROTEIN DOES NOT BIND DUE TO MUTATION OF BASE SEQUENCE

¹⁵N-LABELED λ PHAGE Cro PROTEIN

ARTIFICIAL GENE AND METHOD FOR MUTATING GENE

TECHNICAL FIELD

The present invention relates to an artificial gene and to a method for mutating a gene.

REFERENCE TO AN ELECTRONIC SEQUENCE LISTING

The contents of the electronic sequence listing (740169-000315_SL.txt; Date of Creation: Mar. 10, 2026; and Size: 5,652 bytes) are herein incorporated by reference in their entirety.

BACKGROUND ART

The functions of organisms associated with biodiversity, and particularly the production metabolic functions of algae that produce high concentrations of natural products, e.g., oils, polysaccharides, dyes, and pigments, are receiving attention in a wide range of fields, e.g., energy, food and beverages, nutritional food products, cosmetics, and pharmaceuticals. Genome editing, in which a gene of interest (the target gene) involved in a production is modified, is used to create algal strains that exhibit high productivities.

CITATION LIST

Patent Document

Patent Document 1: Patent Publication JP-A-2018-000129

SUMMARY

Technical Problem

In the process of using wild-type organisms for various purposes, humans have selected and crossbred/bred strains that have phenotypes that are well adapted for a particular purpose and have then used the organisms that exhibit characteristics that are advantageous for achieving the particular purpose. The genomic DNA sequences of these organisms have become relatively easy to analyze in recent years, and it has become possible to clarify the causes of the beneficial phenotypes of these organisms through an understanding of this genetic information. The development of genome editing technology has also made it possible to freely modify a specific gene or DNA region. However, technology for introducing/inserting DNA or a genome editing means into the cell nucleus has not been established for many organisms, and it is not the case that technology for gene recombination/genome editing has been established for all organisms. Moreover, since a genomic DNA gene region of which function has been elucidated is a part of a whole, it is not the case that any beneficial organism can be modified as desired. In addition, the European Court of Justice has issued a ruling that genome editing technology is subject to the same handling restrictions as in the Cartagena Protocol (Cartagena Protocol on Biosafety of the Convention on Biological Diversity, adopted January 2000, at the resumed session of the Conference of the Parties to the Convention on Biological Diversity), which are regulations covering genetically modified organisms, and discussions on the handling continue in individual countries.

Breeding by mutagenesis using, e.g., gamma-ray heavy-ion beam irradiation, DNA modification reagents, etc., which is not regarded as genetic recombination, is therefore still indispensable at present for industrial use (see, for example, Patent Document 1). However, conventional mutation breeding methods do not have a quantitative procedure that directly evaluates the degree of damage to the DNA. As a consequence, the irradiation dose and the treatment amount are determined by using easily scorable phenotype changes, such as mortality rate or pigment formation, as an indirect index of mutation efficiency. In addition, for mutations that are randomly introduced by irradiation, effort and time are required to screen for strains having a target phenotype from among a large number of treatment groups. However, whether a target gene mutation has been produced remains unclear until the screening results are obtained.

The present invention, therefore, provides an artificial gene and a method for mutating a gene which are not subject to gene recombination regulations and which enables the introduction of a local mutation into a target gene and enables the quantitation of this mutation at the time of mutation introduction.

Solution to Problem

As described in detail below with reference to FIG. 5, in the (p, $\alpha_1\gamma$) reaction channel of the $^{15}$N ($^1$H, $\alpha_1\gamma$)$^{12}$C resonant nuclear reaction where $^{16}$O* in the 12.9686 MeV level emits $\alpha$ particles and is deexcited into $^{12}$C* in the 11.6007 MeV first excitation level, $\alpha$ ($^4$He nucleus) and $^{12}$C which have a higher ionization effects than the proton beam are emitted as reaction secondary particles. In addition, a 4.43 MeV gamma-ray is emitted through deexcitation from the $^{12}$C* first excitation level to the ground state in reaction. As a result of extensive research, the present inventors discovered that, when $^{15}$N nucleus located in or near DNA, the emission of the reaction secondary particles which have high ionization effects highly and locally ionize biomolecules near the $^{15}$N and provides a high probability of production of the desired gene mutation in DNA. The present inventors also discovered that, because the 4.43 MeV gamma-ray emitted in every nuclear reaction can be easily detected and because this gamma-ray reflects the amount of gene mutation in the DNA produced by proton beam irradiation, the amount of gene mutation in the DNA can be quantified by detection of the 4.43 MeV gamma-ray during beam irradiation.

With regard to proton beam irradiation to a $^{15}$N-labeled DNA sample or a biological sample such as living cells that contain $^{15}$N_DNA, the present inventors also discovered that, by changing the proton beam energy from the resonance energy to high energy exceeding the resonance energy at a constant energy step width, the $^{15}$N ($^1$H, $\alpha_1\gamma$)$^{12}$C resonant nuclear reaction can be produced in the $^{15}$N distributed throughout in a target sample from the surface into the interior.

An artificial gene, according to an aspect of the present invention, which is based on at least a portion of this knowledge acquired by the present inventors, has a $^{15}$N abundance in bases of at least a portion of a DNA that exceeds a natural abundance. This $^{15}$N abundance is, for example, above 90%, above 91%, above 92%, above 93%, above 94%, above 95%, above 96%, above 97%, or above 98%.

This aspect may contain a $^{15}$N-unlabeled primer sequence and a $^{15}$N-labeled deoxyribonucleotide.

In this aspect, ligation of the artificial gene described in this aspect and another artificial gene may be formed. The other artificial gene may be a vector.

In this aspect, a plurality of biomolecule binding sites may be present, and the gene sequence may be mutated in at least a portion of the plurality of biomolecule binding sites. The biomolecule may be a protein.

An artificial gene, according to an aspect of the present invention, is a $^{15}$N-unlabeled artificial gene and has a plurality of biomolecule binding sites, wherein the gene sequence is mutated in at least a portion of the plurality of biomolecule binding sites, and a $^{15}$N-labeled biomolecule can bind to any of the plurality of biomolecule binding sites. The $^{15}$N-labeled biomolecule may be a protein. The $^{15}$N-labeled biomolecule may be capable of binding at sites, where the gene sequence is not mutated among the plurality of biomolecule binding sites.

A kit, according to an aspect of the present invention, contains the aforementioned $^{15}$N-unlabeled artificial gene and a $^{15}$N-labeled biomolecule that is capable of binding to any of the plurality of biomolecule binding sites.

A method for mutating a gene according to an aspect of the present invention includes labeling DNA with $^{15}$N and irradiating the DNA with a proton beam having energy at which $^{15}$N produces a resonant nuclear reaction.

In the aforementioned aspect, the labeling of the DNA with $^{15}$N may include substituting the N in the DNA with $^{15}$N. Alternatively, the labeling of the DNA with $^{15}$N may include labeling the vicinity of the DNA with $^{15}$N. The labeling of the DNA with $^{15}$N may include the binding of a $^{15}$N-labeled biomolecule to the DNA. The $^{15}$N-labeled biomolecule may be a protein.

In the aforementioned aspect, the DNA in a living cell may be labeled with $^{15}$N.

In the aforementioned aspect, the $^{15}$N abundance in non-DNA cell components in the living cell may be maintained at the natural abundance, and the $^{15}$N abundance in the DNA may be made larger than the natural abundance.

In the aforementioned aspect, the labeling of the DNA with $^{15}$N in the living cell may include the introduction into the living cell of $^{15}$N-labeled deoxyribonucleotide and a glutamine synthetase inhibitor.

In the aforementioned aspect, the labeling of the DNA with $^{15}$N in the living cell may include the introduction into the living cell of $^{15}$N-labeled deoxyribonucleotide and a ribonucleotide reductase inhibitor.

In the aforementioned aspect, the labeling of the DNA with $^{15}$N in the living cell may further include the introduction into the living cell of $^{15}$N-unlabeled glutamine.

In the aforementioned aspect, detecting the resonant nuclear reaction may be further included.

In the aforementioned aspect, an amount of 4.43 MeV gamma-ray may be counted in the detection.

The aforementioned aspect may additionally include calculation, based on the amount of gamma-ray counted, the number of mutations produced in the DNA.

In the aforementioned aspect, the amount of gamma-ray produced in a resonant nuclear reaction induced in a reference sample having a known number of $^{15}$N atoms may be used as a reference in the calculation.

In the aforementioned aspect, the energy for producing a resonant nuclear reaction by $^{15}$N may be varied.

Advantageous Effects of Invention

The present invention can thus provide an artificial gene and a method for mutating a gene which are not subject to gene recombination regulations and which enables the introduction of a local mutation into a target gene and enable the quantitation of this mutation at the time of mutation introduction.

BRIEF DESCRIPTION OF DRAWINGS

FIG. 3 is a diagram that shows the case of the use of a method for mutating a gene by irradiation with a heavy ion beam, which is a conventional art.

FIG. 4 is a diagram that shows an artificial DNA reference sample constructed of 84 base pairs. Figure discloses SEQ ID NOS 1-2, respectively, in order of appearance.

FIG. 11 is a diagram that explains a novel method for carrying out $^{15}$N-labeling of only a target gene or the neighborhood thereof. Figure discloses SEQ ID NOS 20-21, respectively, in order of appearance.

DESCRIPTION OF EMBODIMENTS

Embodiments of the present invention will be described with reference to the appended figures. A feature designated by the same reference sign in individual figures has the same or similar structure.

The element nitrogen N is present in living organisms widely distributed among cell components from proteins, e.g., enzymes, to DNA. In a method for mutating a gene according to the present embodiment, a state is produced in which the isotope $^{15}$N, which is present in living organisms at a natural abundance of 0.364%, is concentrated in and unevenly distributed into a target gene and substantial mutation is produced in the target gene by irradiating the target gene with a proton beam at the energy at which the $^{15}$N ($^{1}$H, $\alpha_{1}\gamma$)$^{12}$C resonant nuclear reaction takes place by $^{15}$N and $^{1}$H.

In the double-stranded DNA that constitutes a gene, five nitrogen atoms are bonded in adenine (A) in the purine ring and as an amino group and two nitrogen atoms are bonded in thymine (T) in the pyrimidine ring, and seven nitrogen atoms are thus present in the adenine-thymine pair (AT pair) in double-stranded DNA. Similarly, five nitrogen atoms are bonded in guanine (G), and three are bonded in cytosine (C), and eight nitrogen atoms are thus present in the guanine-cytosine pair (GC pair) in double-stranded DNA.

Figure 1:
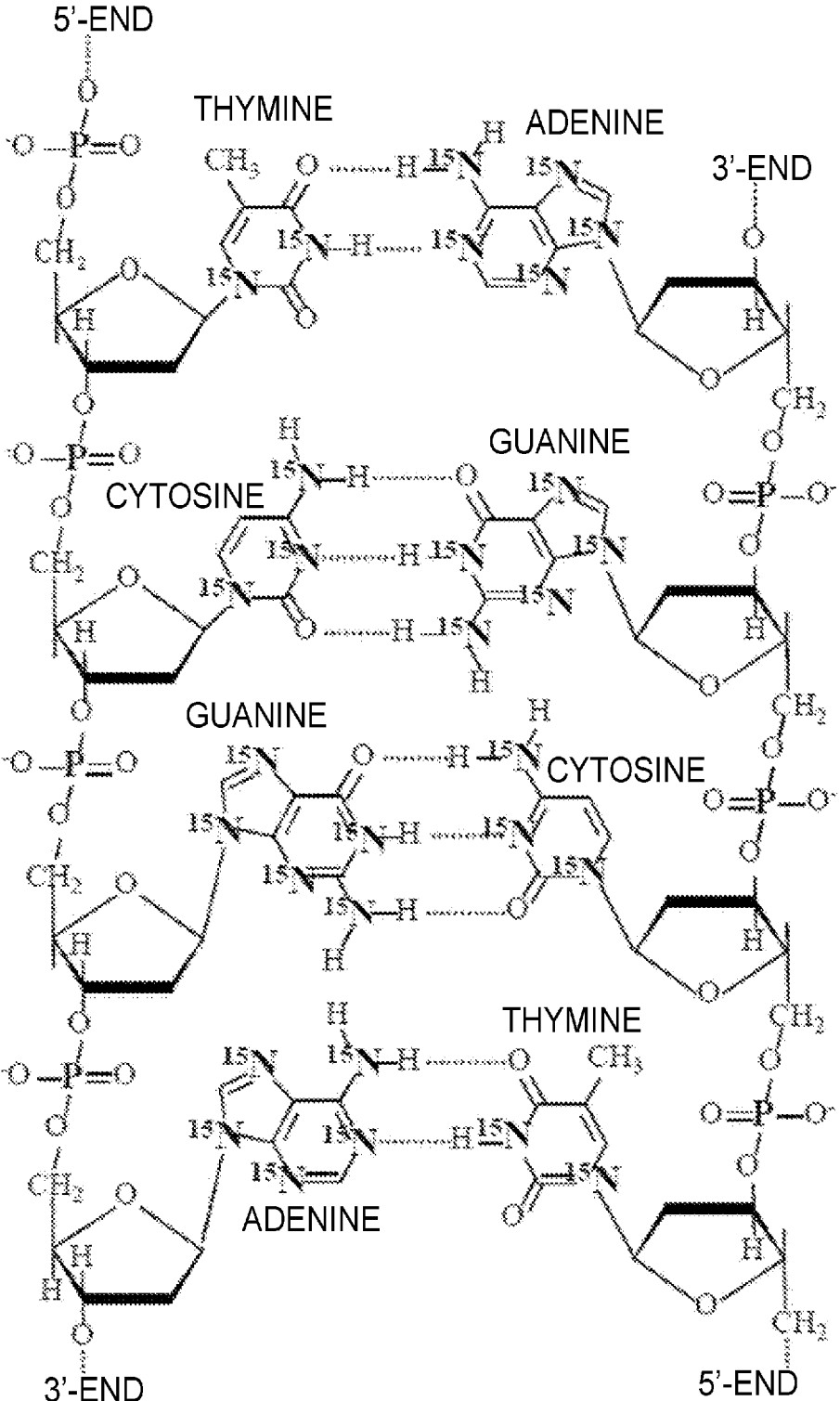
FIG. 1 is a diagram that shows, with reference to a method for mutating a gene according to an embodiment of the present invention, a DNA molecule in which the N presents in each of the base pairs has been replaced with $^{15}$N.

FIG. 1 shows a DNA molecule that possesses $^{15}$N substituted for N in each base pair. The DNA molecule labeled with $^{15}$N by 275.5 times concentrating the isotope ratio at which $^{15}$N is naturally present is shown. $^{15}$N has a natural abundance of 0.364%.

Figure 2:
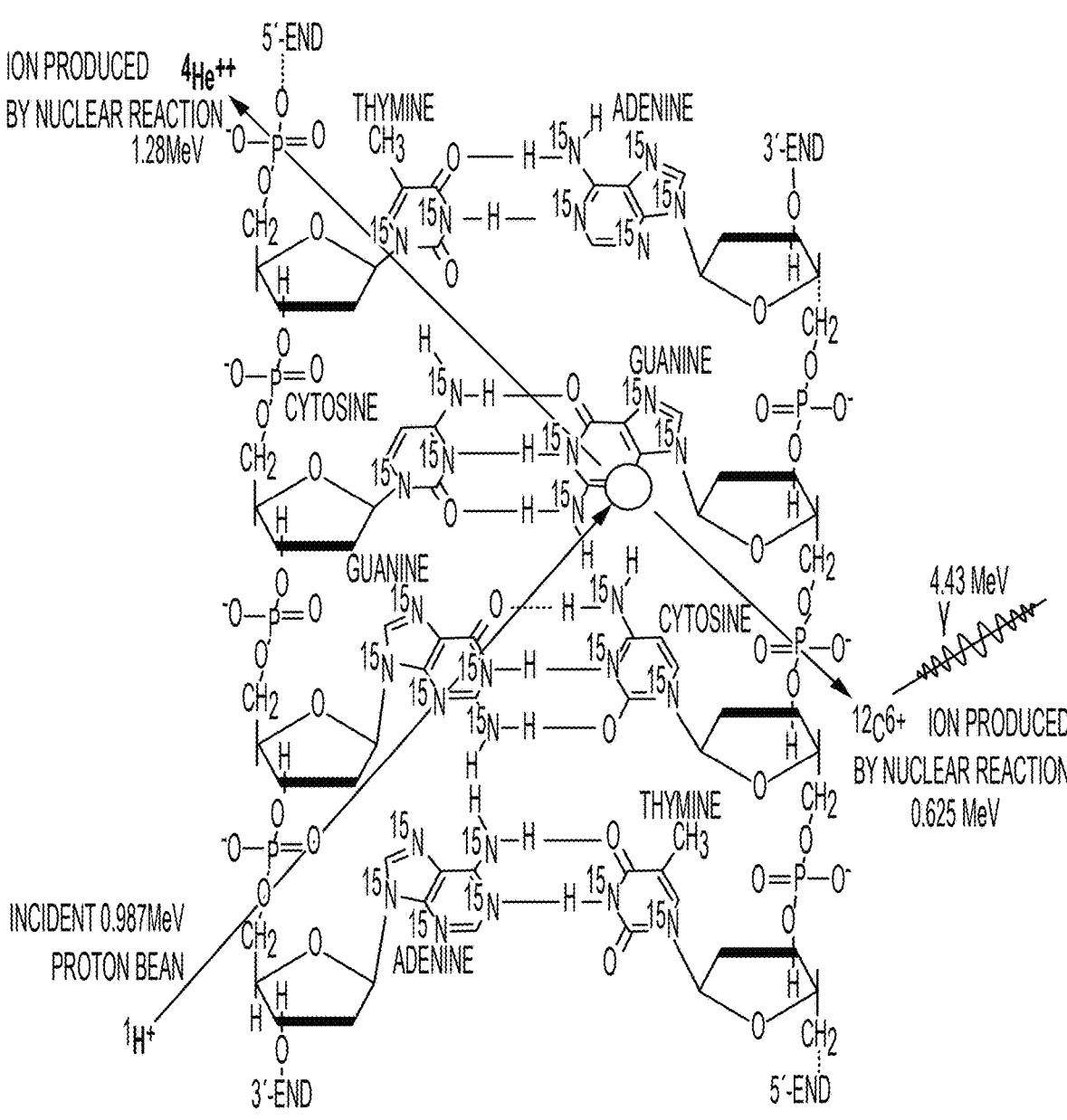
FIG. 2 is a diagram that shows a depiction of the occurrence of a resonant nuclear reaction in a DNA molecule.

FIG. 2 shows a depiction of the occurrence of the resonant nuclear reaction in a DNA molecule. The $^{15}$N ($^{1}$H, $\alpha_{1}\gamma$)$^{12}$C resonant nuclear reaction is taken place by a proton and single $^{15}$N nucleus in the $^{15}$N labelled DNA. The $^{15}$N is extinguished and $^{4}$He nucleus and $^{12}$C nucleus are emitted in an substantially isotropic direction but are just opposite to each other centered on the bonding position of the $^{15}$N atom prior to the reaction. They immediately capture electrons and traverse through the material as ions. They induce high-density electronic excitation of atoms in the vicinity area along the ion trajectory.

The probability of undergoing electronic excitation declines in inverse proportion to the square of the distance from the reaction center and is thus smaller for atoms as the distance of their location from the reaction center becomes far. That is, when $^{15}$N undergoes the resonant nuclear reaction, atoms in the vicinity of the bonding position of the $^{15}$N atom are locally affected by electronic excitation at a high probability. Accordingly, local modification takes place in the vicinity of the $^{15}$N atom in the DNA.

Figure 3:
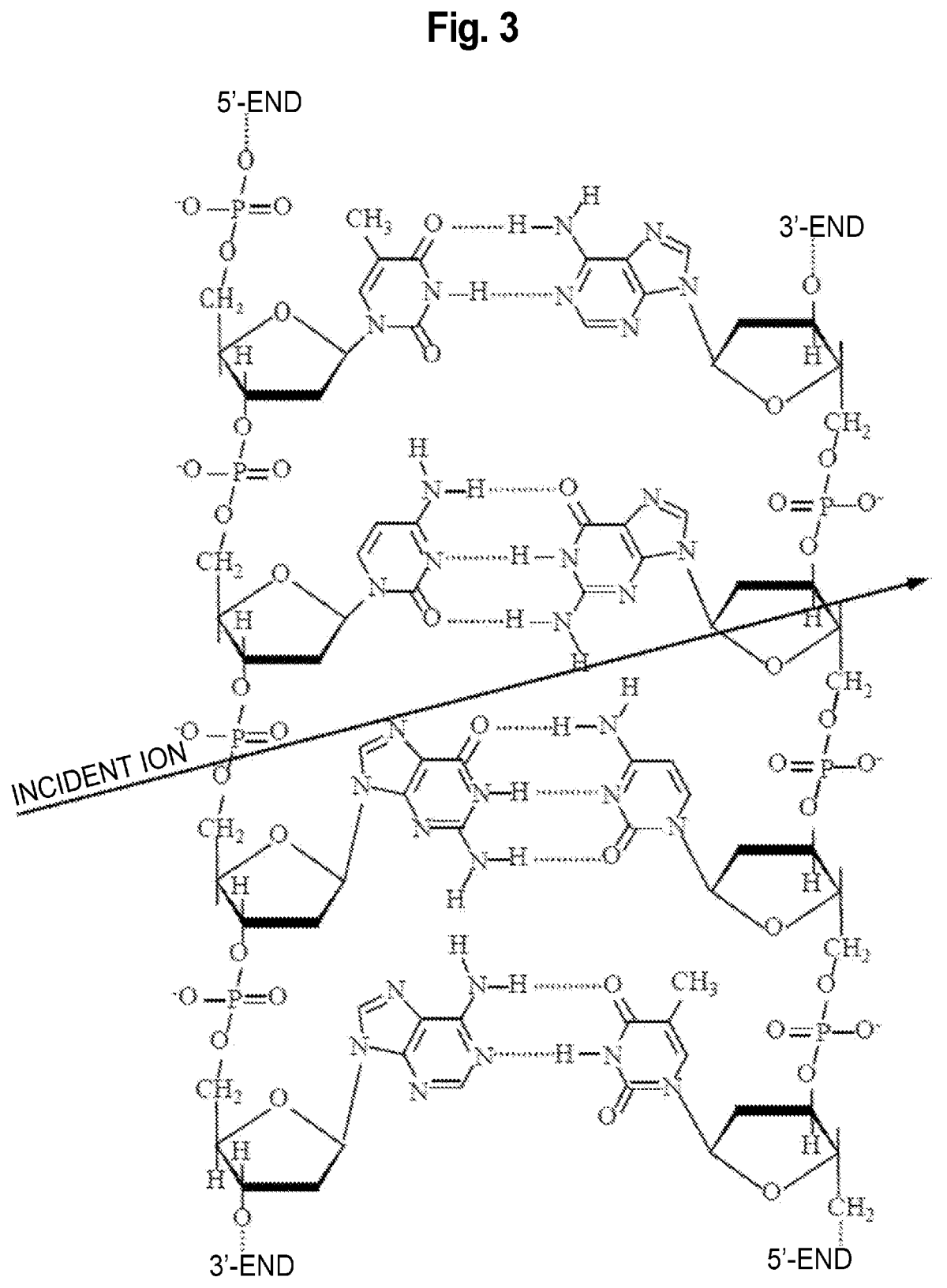

FIG. 3 shows the reference case that has been used conventionally for mutagenesis to gene with irradiation of a heavy ion beam. Since the heavy-ion beam, which is conventionally used for mutagenesis to the gene, is uniformly incident on at a constant density throughout the DNA from the outside of DNA, the probability at which the DNA-atoms in a space in the vicinity of a heavy-ion trajectory suffer electronic excitation, and then the DNA is mutated, is constant throughout the whole area of the DNA.

In contrast to the above-mentioned reference case, the method according to the present embodiment enables the DNA around the biding position of a $^{15}$N atom to be focally mutated at a high probability by raising the isotopic ratio of $^{15}$N in or in the vicinity of the target gene.

The technique in the present embodiment of raising the isotopic ratio of $^{15}$N in a target gene or neighborhood thereof is an art that directly utilizes the $^{15}$N, natural abundance of which is 0.364% and is also present in living organisms. In addition, the $^{15}$N ($^{1}$H, $\alpha_{1}\gamma$)$^{12}$C resonant nuclear reaction also takes place in collision of a proton beam with the target $^{15}$N presented in DNA of the organisms living on the surface of the Earth, where proton beam, which is the most probable hadron component in the cosmic rays in the sea level, is randomly poured on. The application of the $^{15}$N ($^{1}$H, $\alpha_{1}\gamma$) $^{12}$C resonant nuclear reaction in the present embodiment reproduces the same radiation effects as naturally induced on biological cells.

That is, the series of technique in the present embodiment: raising the isotopic ratio of $^{15}$N in a target gene or neighborhood thereof, and a rise thereby in the probability of mutation in the target gene when the $^{15}$N ($^{1}$H, MY)$^{12}$C resonant nuclear reaction is induced by proton beam irradiation to the $^{15}$N-labeled living cells, are nothing more than accelerating the same processes as of life on the Earth, which has been exposed to nature and suffered mutation in its gene information-since its appearance on the Earth. The principle of the fundamental mechanism in the method of the present embodiment is not at all different from the conventional methods to generate mutant strains by exposure to radiation (UV, X-ray, gamma-ray, and heavy-ion). Accordingly, since the principle in the method to generate mutation of a gene according to the series of technique in the present embodiment is different in principle from the genetic-recombination technique, the present method, which is not covered by the regulation on the genetic-recombination technology, enables one to generate the substantial mutation in a target gene.

A $^{15}$N-labeled DNA reference sample having a precisely specified the number of $^{15}$N atoms must be developed in order to quantitate mutation produced by the proton beam irradiation in a DNA sample, in which the isotopic ratio of $^{15}$N is raised in a target gene or in the vicinity of the target gene in a living cell.

The $^{15}$N-labeled DNA reference sample supports the acquisition of calibration data between the $^{15}$N concentration in a DNA and the yields of 4.43 MeV gamma-rays emitted by the $^{15}$N ($^{1}$H, $\alpha_{1}\gamma$)$^{12}$C resonant nuclear reaction. Acquisition of calibration data of the yields of 4.43 MeV gamma-ray makes it possible—by detecting the yields of 4.43 MeV gamma-ray emitted by the resonant nuclear reaction at the same time as proton beam irradiation to the $^{15}$N-labeled living cell and comparing this with the calibration values of the yields—to quantitate the number of mutations generated in the DNA in a living cell.

In the method for mutating a gene according to the present embodiment, a reference sample was constructed by the artificial synthesis by a polymerase chain reaction of DNA composed of $^{15}$N-labeled base pairs. The reference sample of the constructed artificial DNA is desirably composed of a base sequence important in molecular biology, biochemistry, or biofunctionality.

FIG. 4 is a diagram that shows an artificial DNA reference sample constructed of 84 base pairs. The artificial DNA reference sample is constructed, for example, using the following method. An OR_WT_F oligonucleotide is synthesized by a polymerase chain reaction from a $^{15}$N-unlabeled, i.e., containing $^{14}$N at the natural abundance of 99.636%, OR_primer_F primer having the sequence structure of TACGTTAAATC at the 5'-end, and from 73 $^{15}$N-labeled, i.e., containing $^{15}$N at an abundance of at least 98%, deoxyribonucleoside 5'-triphosphates ($^{15}$N-labeled dNTPs). An OR_WT_R oligonucleotide is also synthesized by a polymerase chain reaction from a $^{15}$N-unlabeled OR_primer_R primer having the sequence structure of TGCAAC-CATT at the 5'-end, and from 74 $^{15}$N-labeled dNTPs. A $^{15}$N-labeled double-stranded DNA oligonucleotide, i.e., $^{15}$N-labeled OR_DNA, is formed by the formation of base pairs between OR_WT_F and OR_WT_R by hydrogen bonding. This is used as the reference sample.

The $^{15}$N-labeled OR_DNA is constructed of a total of 84 DNA base pairs (84 bps) from the $^{15}$N-unlabeled primers OR_primer_F/_R and $^{15}$N-labeled dNMPs (deoxyribonucle-otide 5'-monophosphates). Excluding the primer, the base sequence itemization for the 73 bps in OR_WT_F is $^{15}$N-labeled dAMP: 19, $^{15}$N-labeled dTMP: 22, $^{15}$N-labeled dGMP: 17, and $^{15}$N-labeled dCMP: 15. Excluding the primer, for the 74 bps in OR_WT_R this is $^{15}$N-labeled dAMP: 23, $^{15}$N-labeled dTMP: 20, $^{15}$N-labeled dGMP: 16, and $^{15}$N-labeled dCMP: 15. This is summarized in the following Table 1.

secondary reaction particles having a high ionization effects does not occur in the (p, $\gamma_0$) reaction channel. When $^{15}$N is present within DNA or in the vicinity thereof, the emission of highly ionizing reaction secondary particles exercises a locally high ionization effects on the biomolecules in the vicinity of the $^{15}$N and achieves the effect of providing a high probability of the generation of a desired gene mutation in the DNA. In addition, the 4.43 MeV gamma-ray emitted in every nuclear reaction can be easily detected, and this gamma-ray reflects the amount of gene mutation in the DNA that is produced by the irradiation with the proton beam. As

TABLE 1

|  | OligoDNA OR_DNA 84 base pairs | Oligonucleotide OR_WT_F 73 bases | Primer OR_primer_F 11 bases | Oligonucleotide OR_WT_R 74 bases | Primer OR_primer_R 10 bases |
|---|---|---|---|---|---|
| dAMP | 49 | 19 | 4 | 23 | 3 |
| dTMP | 49 | 22 | 4 | 20 | 3 |
| dGMP | 35 | 17 | 1 | 16 | 1 |
| dCMP | 35 | 15 | 2 | 15 | 3 |
| Number of nitrogen atoms | 623 | 269 | 39 | 280 | 35 |
| $^{15}$N isotope count | 538.29 | 263.62 | 0.14 | 274.4 | 0.13 |
| Molecular weight (g/mol) 98% $^{15}$N label purity | 52,467.00 | 26,234.64 | | 26,232.36 | |
| Molecular weight (g/mol) 100% $^{15}$N label purity | 52,477.95 | 26,240.00 | | 26,237.95 | |

The total number of N ($^{14}$N+$^{15}$N) contained in the $^{15}$N-labeled OR_DNA is 623. The degree of $^{15}$N purity is ≥98%, and the isotopic ratio of $^{15}$N to $^{14}$N varies in accordance with this degree of purity. When the degree of $^{15}$N purity is 98%, the number of $^{15}$N in the $^{15}$N-labeled OR_DNA is 538.29. At an ideal 100% degree of $^{15}$N purity, the number of $^{15}$N in the $^{15}$N-labeled OR_DNA has a maximum of 549.27, whose value corresponds to 88.17% of the total number of nitrogen atoms (refer to Table 1). The molecular weight of the $^{15}$N-labeled OR_DNA also depends on the degree of $^{15}$N purity and is ≥52, 467 g/mol and has a maximum of 52, 477.95 g/mol.

Figure 5:
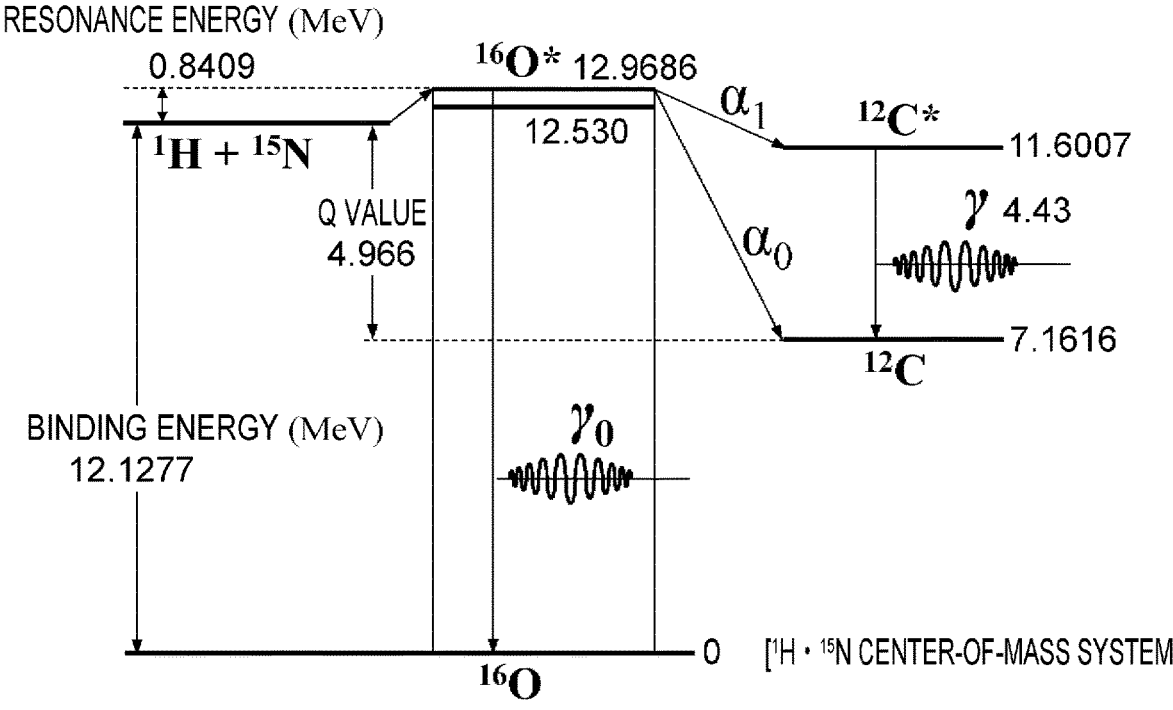
FIG. 5 is a diagram that shows the $^{15}$N ($^1$H, $\alpha_1\gamma$)$^{12}$C resonant nuclear reaction.

FIG. 5 shows the $^{15}$N ($^1$H, $\alpha_1\gamma$)$^{12}$C resonant nuclear reaction. When nuclei collide at 0.8409 MeV of a proton beam in the center-of-mass system (0.987 MeV in the laboratory system) accords with an energy difference between the nucleic binding energy of 12.1277 MeV in the $^{15}$N and proton system and an excitation energy level of 12.9686 MeV in the $^{16}$O* compound nucleus, the nuclear reaction occurs resonantly to produce $^{16}$O* compound atomic nucleus. The $^{16}$O* in the 12.9686 MeV level immediately brings about three kinds of reaction channels: the first reaction channel in which deexcitation to the 11.6007 MeV first excitation level of $^{12}$C* occurs with the emission of an a particle; the second reaction channel in which deexcitation to the 7.1616 MeV ground state of $^{12}$C occurs with the emission of an a particle; and a third reaction channel in which deexcitation to the 0 MeV ground state of 16O occurs with the emission of only a gamma-ray. These are respectively represented by the nuclear reaction formulae (p, $\alpha_1\gamma$), (p, $\alpha_0$), and (p, $\gamma_0$).

The (p, $\alpha_1\gamma$) reaction channel used in the present embodiment has the following characteristic features: an a ($^4$He atomic nucleus), which has a higher ionization effects than the proton beam, and $^{12}$C are emitted as secondary reaction particles; and a 4.43 MeV gamma-ray is emitted in every reaction by the deexcitation from the first excitation level of $^{12}$C* to the ground state. Gamma-ray emission does not occur in the (p, $\alpha_0$) reaction channel, and emission of a a consequence, The detection of the 4.43 MeV gamma-rays when beam irradiation is performed achieves the effect of enabling quantitation of the amount of gene mutation in the DNA.

The resonance energy with the $^{16}$O* second excitation level is much lower than the Coulomb barrier potential in the nuclear collision of the two atoms. Due to this, when the nuclear collision energy of the two atoms deviates from the resonance energy, exceeding the 300 eV resonance energy width defined as the width of the second excitation level of the $^{16}$O* compound atomic nucleus, the reaction cross-section sharply decreases. That is, the proton beam incident at the resonance energy on the $^{15}$N-labeled OR_DNA causes the generation of the $^{15}$N ($^1$H, $\alpha_1\gamma$)$^{12}$C resonant nuclear reaction only within the range in which fluctuations in the incident energy fall within the resonance energy width.

Figure 13:
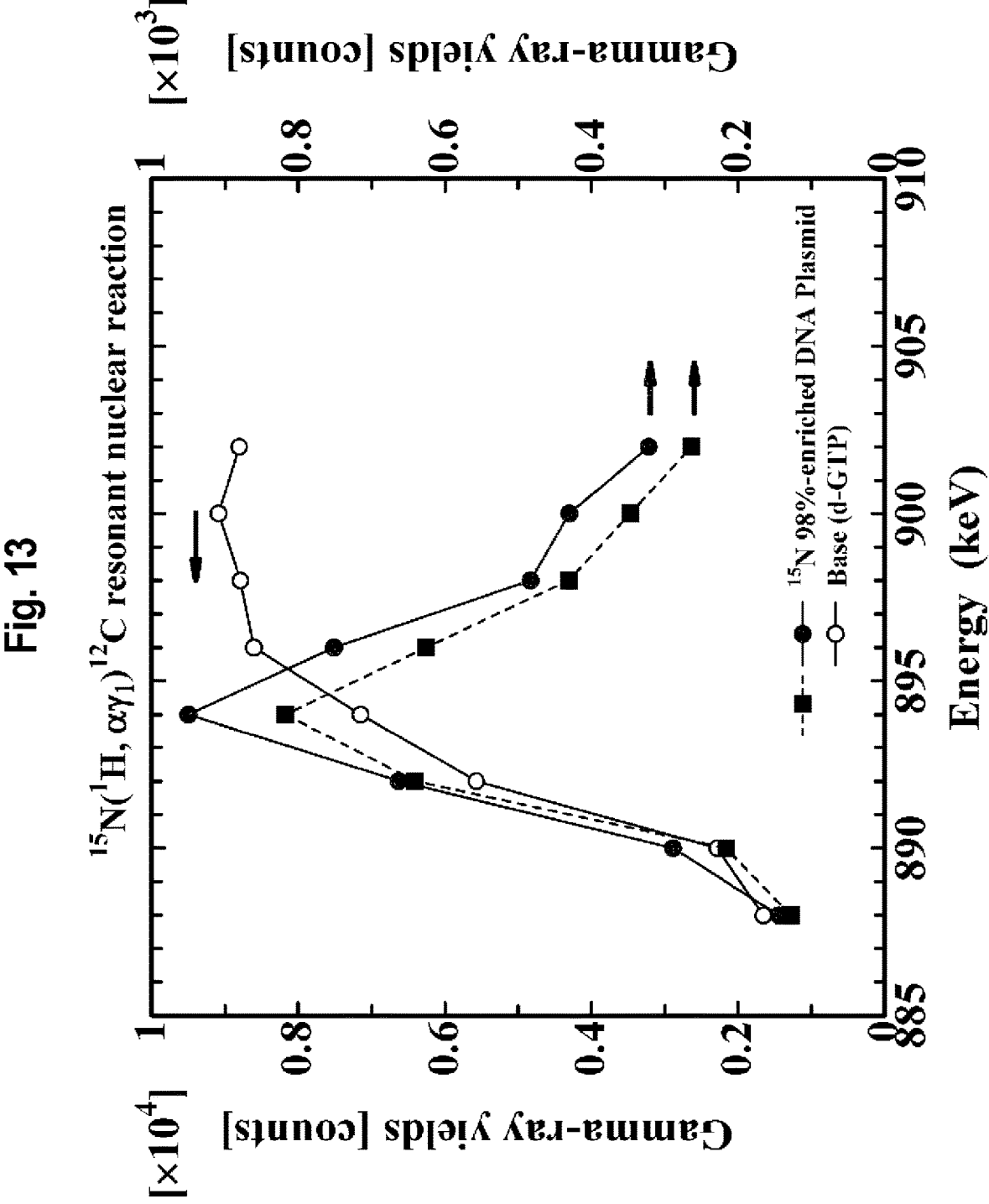
FIG. 13 is a graph that shows the resonance curve for the $^{15}$N (p, $\alpha_1\gamma$)$^{12}$C resonant nuclear reaction for a $^{15}$N_pUC4-KIXX plasmid sample.

In actual proton beam irradiation, the resonance energy width is determined by a convolution integration operation between the resonance energy width and the energy distribution of the proton beam, typically about 1 keV, and the proton beam irradiation energy is determined by adding the energy loss during the passage of protons through the substance to the resonance energy. That is, in the proton beam irradiation of a biological sample such as a $^{15}$N-labeled DNA sample or a living cell containing $^{15}$N_DNA, the $^{15}$N ($^1$H, $\alpha_1\gamma$)$^{12}$C resonant nuclear reaction can be produced everywhere in the $^{15}$N distributed in a target sample from the surface into the interior, by causing the proton beam energy to change from the resonance energy to high energy exceeding the resonance energy, for example, by causing a change at a prescribed energy step width. The energy change width and the step width may be selected in correspondence to the target sample, and the resonance curve of the $^{15}$N ($^1$H, $\alpha_1\gamma$)$^{12}$C resonant nuclear reaction may then be acquired and determined. Refer, for example, to FIG. 13.

The a and $^{12}$C* produced by the $^{15}$N ($^1$H, $\alpha_1\gamma$)$^{12}$C resonant nuclear reaction are emitted in opposite directions from each other, and when emission occurs in the same direction as the incident direction of the proton beam, the kinetic energy assumes a maximum value E(max) and becomes $E_c$(max)=0.6252 MeV and $E_{He}$(max)=1.2806 MeV for $^{12}$C* and a, respectively. In addition, when $^{12}$C* and a are emitted in the opposite direction from the incident direction of the proton beam, the kinetic energy assumes a minimum value E(min) and becomes $E_c$(min)=0.1437 MeV and $E_{He}$(min)=0.7991 MeV. $^{12}$C* and a capture electrons immediately after emission to become $^{12}$C and $^4$He ions and proceed through the substance.

The $^{12}$C and $^4$He ions, constantly having values in these energy ranges, pass through the $^{15}$N-labeled OR_DNA sample. Neighboring atoms along their ion trajectory, particularly neighboring atoms with a radius from at least 5 nm to not more than 10 nm, suffer electronic excitation. Even when proton beam irradiation is carried out at higher energy than the resonance energy-considering in advance that the target sample is not the $^{15}$N-labeled OR_DNA sample, but a biological sample having a cell wall or organelles, e.g., eukaryotic unicellular algae, and energy loss occur when the protons pass through, e.g., the cell wall or organelles—a characteristic feature of the present method is that the reaction-generated $^{12}$C and $^4$He ions are emitted at certain energies, regardless of the irradiation energy of the proton beam, in the $^{15}$N ($^1$H, $\alpha_1\gamma$)$^{12}$C resonant nuclear reaction between the proton beam and $^{15}$N-labeled DNA or a DNA-adjacent $^{15}$N-labeled sample, and neighboring atoms along their ion trajectory suffer excitation at a certain intensity.

In addition, the electronic excitation from the reaction-generated $^{12}$C and $^4$He ions is given by the linear energy transfer (LET (MeVcm$^2$/g)) and varies over the energy range in which the reaction-generated $^{12}$C and $^4$He ions are emitted. The LET to carbon C, which is one of the constituent elements of the target sample, is at least $2.51\times10^3$ MeVcm$^2$/g and a maximum of $4.70\times10^3$ MeVcm$^2$/g for the reaction-generated $^{12}$C ion and is at least $1.73\times10^3$ MeVcm$^2$/g and a maximum of $1.99\times10^3$ MeVcm$^2$/g for the reaction-generated $^4$He ion. These values are at least 17.2-times and a maximum of 27.1-times higher than the LET when protons traverse the $^{15}$N-labeled OR_DNA sample at the resonance energy. Accordingly, a characteristic feature of the present method is that, for biological samples and particularly the $^{15}$N-labeled OR_DNA sample, electronic excitation by the ions produced by the $^{15}$N ($^1$H, $\alpha_1\gamma$)$^{12}$C resonant nuclear reaction is very significantly higher than electronic excitation by proton beam irradiation, and the selective introduction of substantial mutation is thus made possible by the $^{15}$N-labeling of a target gene.

The LET values for the reaction-generated $^{12}$C and $^4$He ions are at least 4.3-times and a maximum of 8.1-times higher than for typical heavy ion irradiation (for example, the $0.58\times10^3$ MeVcm$^2$/g, which is the LET to C in irradiation with the 320 MeV C ion). Furthermore, because the reaction-generated $^{12}$C and $^4$He ions are emitted from the DNA interior or from the vicinity of the DNA, the mutation is produced—in the $^{15}$N-labeled OR_DNA sample or a living cell labeled with $^{15}$N in the DNA or in the vicinity of the DNA—at a high probability in a gene near $^{15}$N by a single $^{15}$N ($^1$H, $\alpha_1\gamma$)$^{12}$C resonant nuclear reaction. The present method, therefore, enables the direction quantitation of the number of gene mutations produced in the vicinity of $^{15}$N by counting the 4.43 MeV gamma-rays emitted from the first excitation level of the $^{12}$C reaction product nucleus.

The mutation produced in the $^{15}$N-labeled OR_DNA sample by proton beam irradiation is different from a biological sample having a DNA repair function, and DNA repair is not carried out. Accordingly, the pure physical mutation status induced by proton beam irradiation is clarified by analyzing the mutation of the $^{15}$N-labeled OR_DNA sample. One method for analyzing the mutation produced in the $^{15}$N-labeled OR_DNA sample is to determine the presence/absence of DNA cleavage by utilizing a cyclic plasmid vector or DNA having a cyclic shape that is present in the cytoplasm of, e.g., bacteria.

Figure 6:
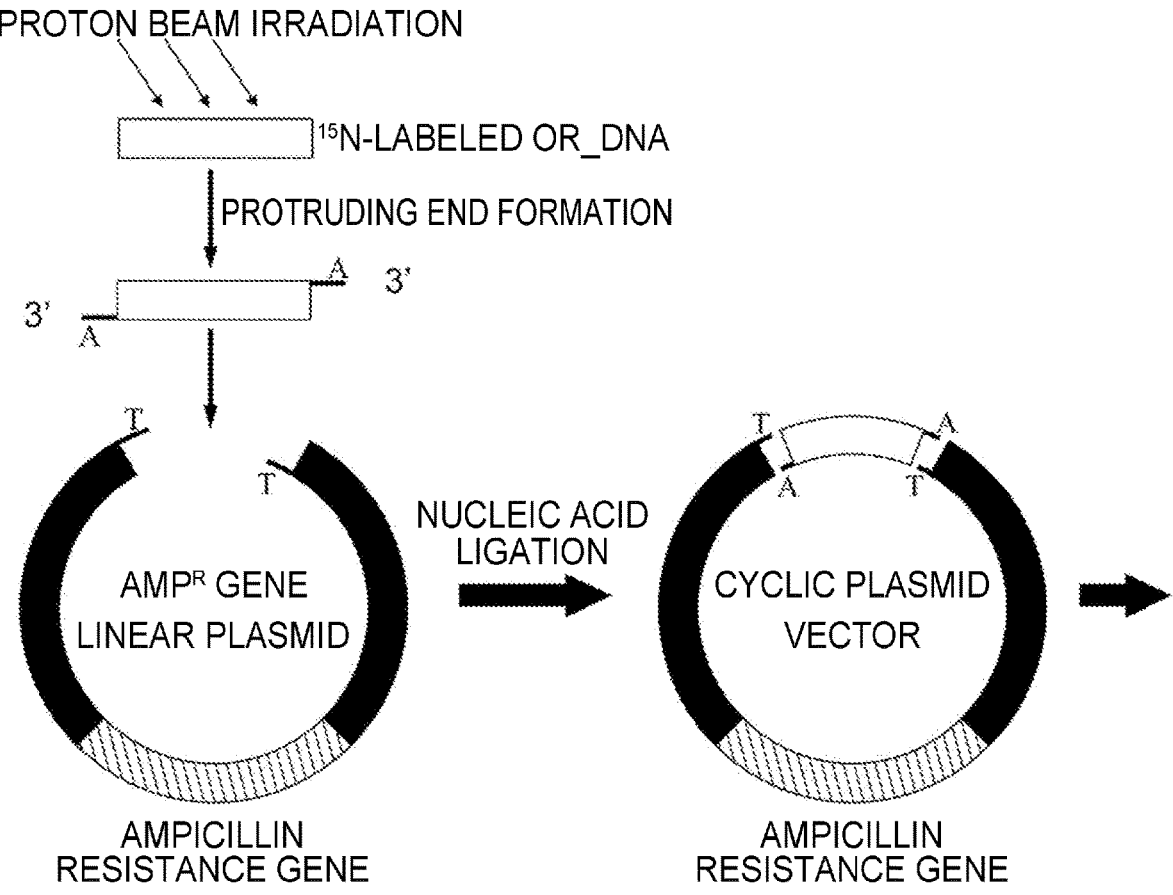
FIG. 6 is a schematic diagram of a method for determining the presence/absence of DNA cleavage.

FIG. 6 shows an artificial gene provided by the ligation of the artificial gene shown in FIG. 4 into a different artificial gene and also shows an outline of a method for determining the presence/absence of DNA cleavage. A cyclized plasmid vector is produced by ligating the $^{15}$N-labeled OR_DNA into an artificially synthesized linear plasmid (T-vector pMD19, 2,692 base pairs) that incorporates an E. coli gene that provides resistance to ampicillin, a β-lactam-type antibiotic used to treat infections, and this cyclized plasmid vector is introduced into a culture medium of E. coli. The cyclized plasmid vector is taken up by the E. coli, and the ampicillin-resistant E. coli propagate. When the $^{15}$N-labeled OR_DNA has been preliminarily cleaved by proton beam irradiation, the plasmid vector does not become cyclic and is degraded in the E. coli cell and does not become a stable gene and the E. coli is then not resistant to ampicillin and dies. For the cyclic plasmid vector in which the $^{15}$N-labeled OR_DNA is ligated, E. coli growth is slower as more cleaved $^{15}$N-labeled OR_DNA is contained. Each of the following samples was ligated into T-vector pMD19: $^{15}$N-labeled OR_DNA sample, $^{15}$N-unlabeled OR_DNA sample, and $^{15}$N-labeled OR_DNA for non-proton-beam-irradiation; and each was introduced into the ampicillin-containing culture medium, and the number of E. coli colonies was compared. With the $^{15}$N-labeled OR_DNA sample, DNA mutation is produced by the proton beam and the $^{15}$N ($^1$H, $\alpha_1\gamma$)$^{12}$C resonant nuclear reaction. With the $^{15}$N-unlabeled OR_DNA sample, DNA mutation is produced by only the proton beam. DNA mutation is not produced with the non-proton-beam-irradiated sample. This evaluation method clarifies the relative frequency of introduction of DNA mutation by the proton beam irradiation of the $^{15}$N-labeled OR_DNA.

The following is a method for more directly analyzing the status of cleavage of the $^{15}$N-labeled OR_DNA by proton beam irradiation: introducing a phosphate group containing the $^{32}$P radioisotope and separating the fragments by electrophoresis at a resolution of 1 base. This method enables the identification of the extent of cleavage in one of the DNA strands.

Figure 7:
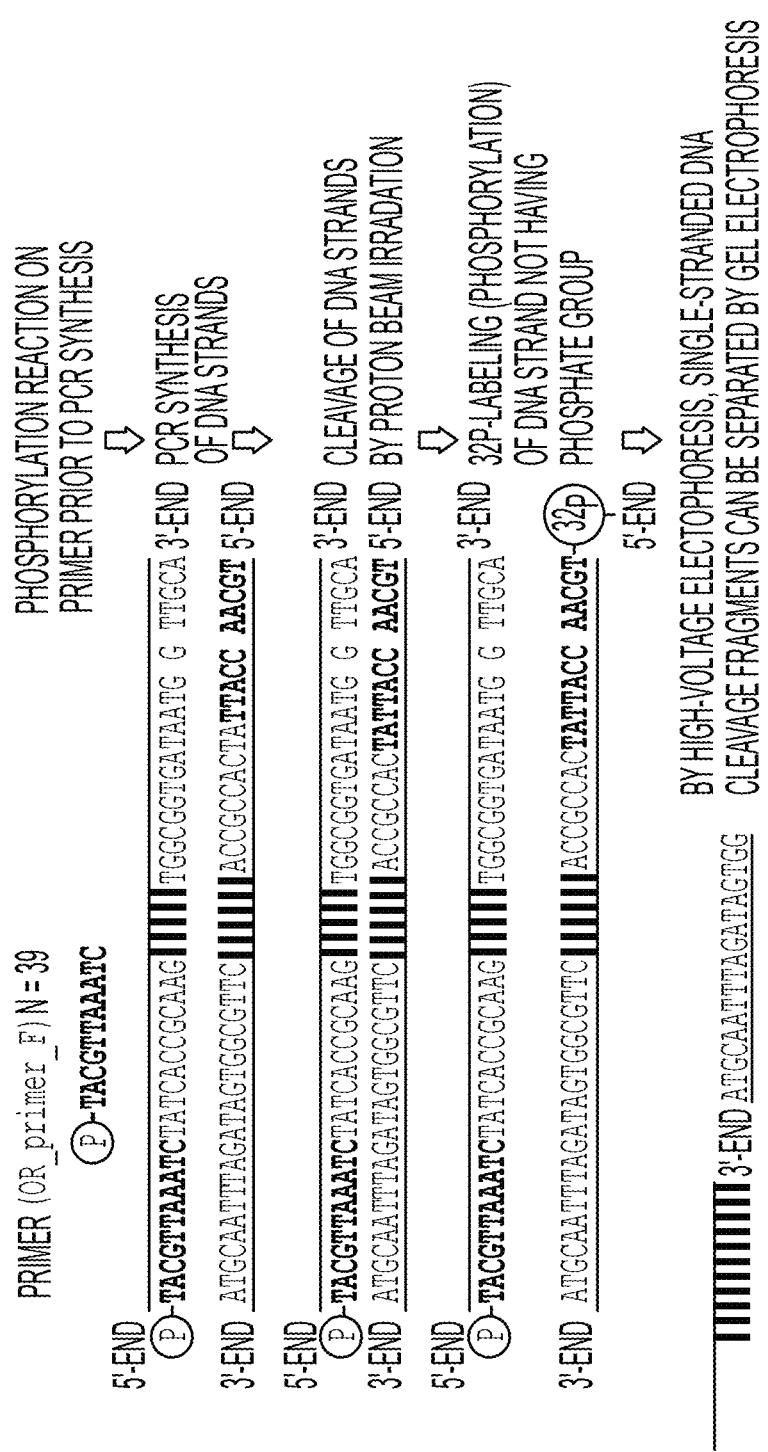
FIG. 7 is a diagram that shows an outline of a method for identifying the extent of cleavage in one strand of DNA strands. Figure discloses SEQ ID NOS 3-19, respectively, in order of appearance.

FIG. 7 shows an outline of a method for identifying the extent of cleavage in one strand of DNA strands. One of the primers, OR_primer_F or OR_primer_R, is first phosphorylated with ATP prior to PCR sample synthesis of the $^{15}$N-labeled OR_DNA and during PCR sample synthesis, a DNA fragment is synthesized that has the phosphate group attached only to the 5'-end of one DNA chain. After proton beam irradiation, only the DNA chain to which the phosphate group is not attached is labeled with 32p using [γ?$^{32}$P]-ATP. When high-voltage electrophoresis at a low salt concentration on a urea-containing thin gel is used to separate the DNA in a single-stranded state (denatured state) while heating, the DNA can be distinguished at a single base difference. Since a single base difference can be distinguished by gel electrophoresis, it is possible to distinguish whether cleavage could be random or is prone to occur only in the vicinity of certain specific bases.

When the DNA within a living cell is labeled with $^{15}$N, only the DNA is $^{15}$N-labeled by discriminating between the nitrogen that constitutes the DNA and non-DNA nitrogenous intracellular molecules that constitute the living cell, for example, the nitrogen atoms present in protein, e.g., proteins that form the cell and enzymes that regulate metabolic functions, or the nitrogen present in the RNAs that carry out various functions in the cell, e.g., the ribosomal RNA that forms the ribosomes, the transfer RNA that transports amino acids, and the messenger RNA that specifies amino acid sequences at the ribosome.

The nitrogen in a cell is utilized in diverse nitrogenous organic compounds, e.g., amino acids, nucleotides, proteins, nucleic acids (DNA, RNA), and some lipids. For all of these nitrogenous organic compounds, an initial organic nitrogenous compound is produced by the glutamine synthetase-mediated reaction with glutamic acid of inorganic nitrogen in the form of the ammonium ion $NH_4^+$ to fix the same in an organic compound as glutamine (ammonia assimilation). An amino group is transferred from glutamine to 2-oxoglutaric acid by glutamate synthase to produce two molecules of glutamic acid. Numerous nitrogenous organic compounds are synthesized by the direct modification of the thusly produced glutamine and glutamic acid or by amino group transfer reactions.

Figure 8:
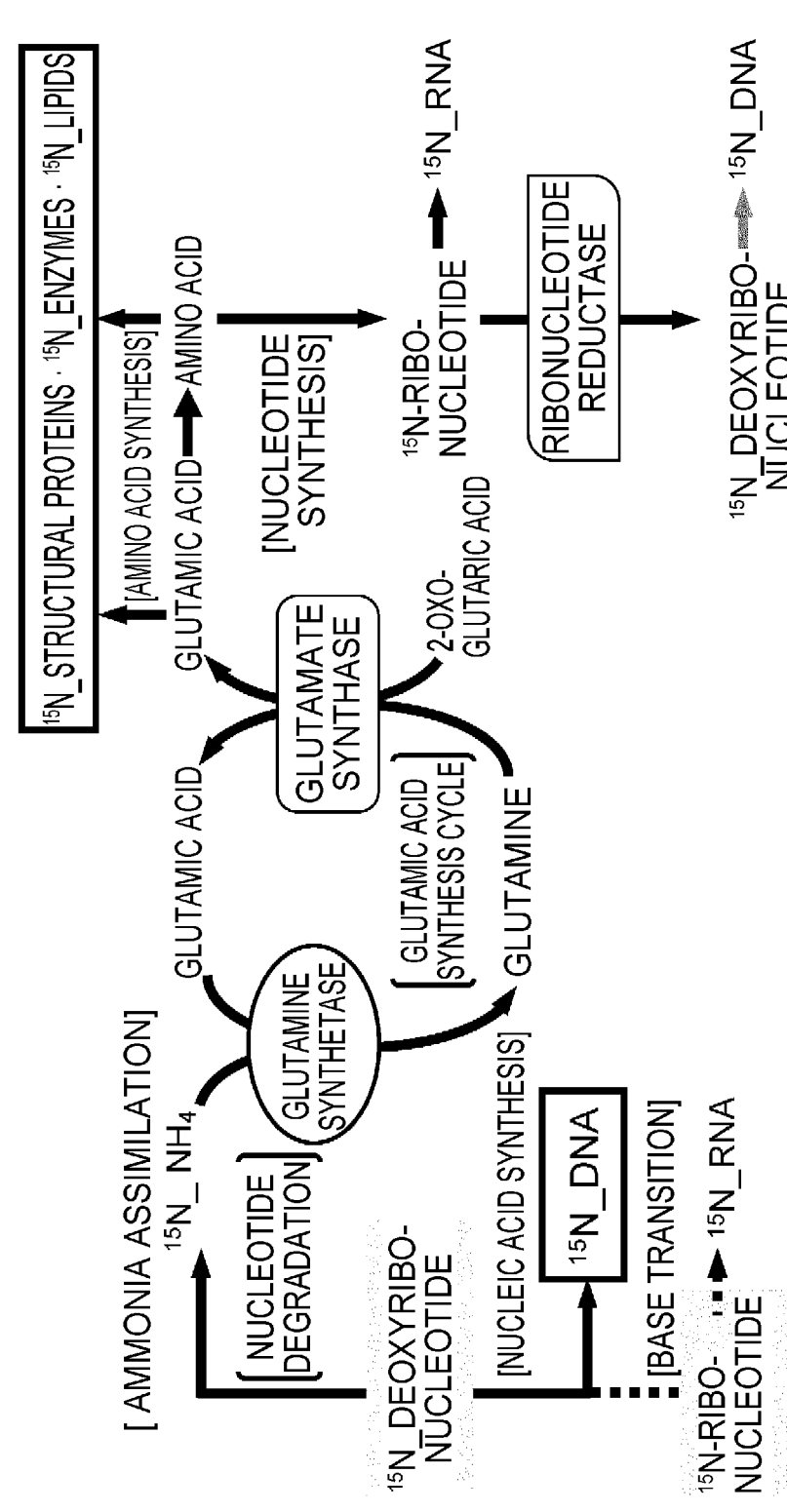
FIG. 8 is a diagram that illustrates the synthesis of nitrogenous organic compounds in the cell.

FIG. 8 shows synthesis pathways for nitrogenous organic compounds in the cell. Nitrogenous compounds are degraded in the cell back to ammonia for recycling. Amino acids are used in the synthesis of structural proteins, enzymes, nucleic acids, and lipids for various uses. On the other hand, in the case of DNA, DNA synthesis proceeds from deoxyribonucleotides by the successive transfer of genetic information. When an artificially synthesized $^{15}$N-labeled deoxyribonucleotide is introduced into the culture medium, it is taken up by the cell, and a portion is degraded, and the ammonium ion is synthesized, and protein synthesis is begun. In order to carry out the $^{15}$N-labeling of only DNA, methionine sulfoximine (MSX), which is an inhibitor of glutamine synthetase, is introduced to inhibit this process so $^{15}$N-labeled protein is not synthesized.

Figure 9:
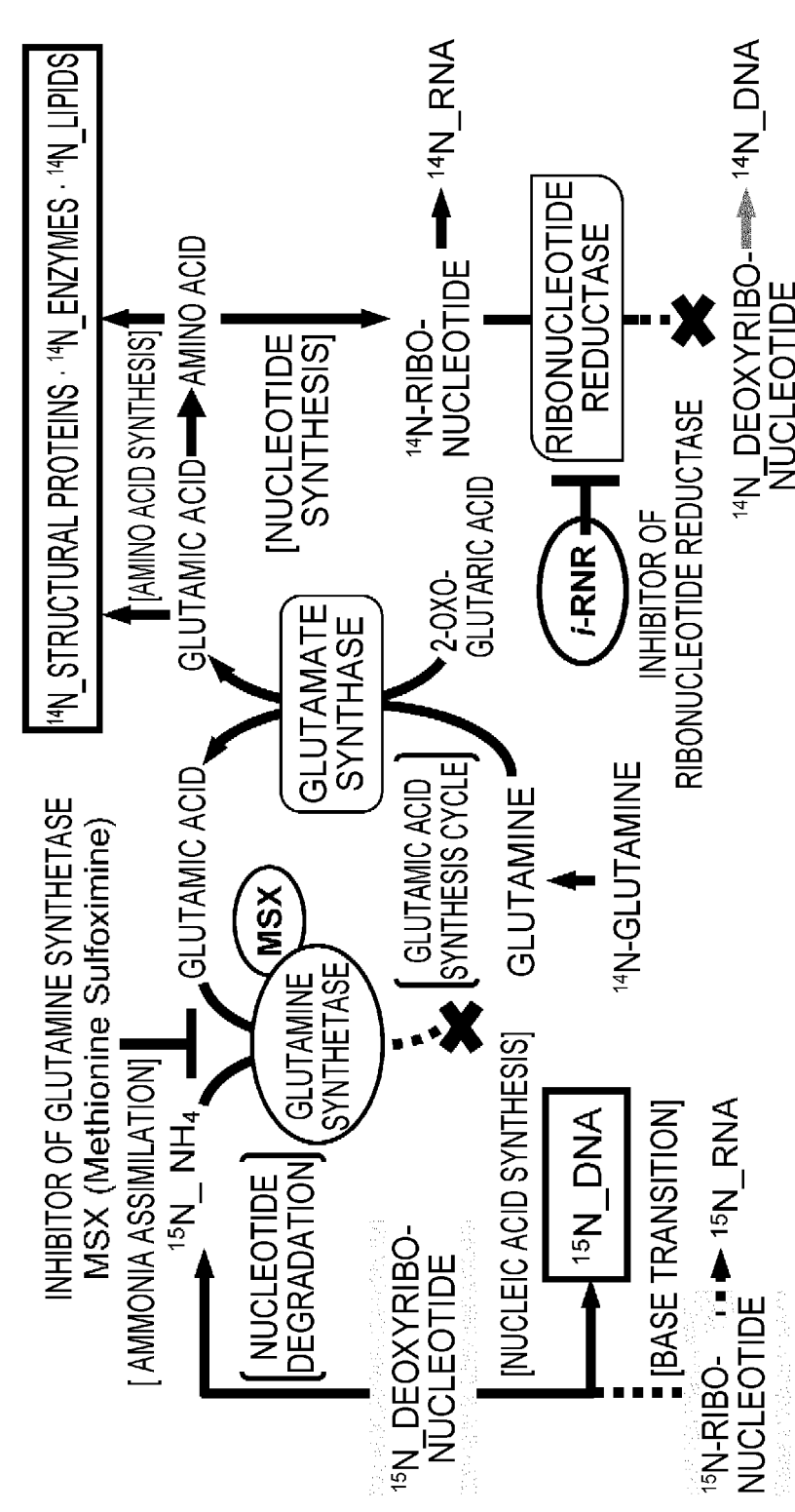
FIG. 9 is a diagram that explains a novel method for the $^{15}$N-labeling of only the nucleic acids in a cell in the case of the administration of MSX and $^{15}$N-unlabeled glutamine.

FIG. 9 shows a novel method for the $^{15}$N-labeling of only the nucleic acids in a cell in the case of the administration of MSX and $^{15}$N-unlabeled glutamine. Glutamic acid and ammonia for the amino group bind to the active site of glutamine synthetase to synthesize glutamine, and the glutamine is released from the glutamine synthetase. However, the structural formula for MSX contains the HN=S=O structure, and this resembles the $H_2N$—CH=O in the structural formula for glutamine. In addition, as MSX has a strong active site, if glutamic acid and ammonia bind to it, they cannot be released from it and formation of glutamine is inhibited. That is, the cycle of glutamic acid synthesis by glutamate synthase from glutamine is interrupted, and $^{15}$N-labeled protein is then not synthesized. However, $^{15}$N-unlabeled glutamine is added to the culture medium so as not to interrupt the synthesis of proteins, which are required for numerous purposes. This results in the synthesis of structural proteins, enzymes, and some DNA. RNA in which the $^{14}$N abundance is 99.637%. Of the $^{15}$N-labeled deoxyribonucleotide taken up into the cell, the remaining $^{15}$N-labeled deoxyribonucleotide not committed to ammonia synthesis is used to synthesize DNA, and as a consequence, the performance of $^{15}$N-labeling in the cell is limited to only DNA.

Figure 10:
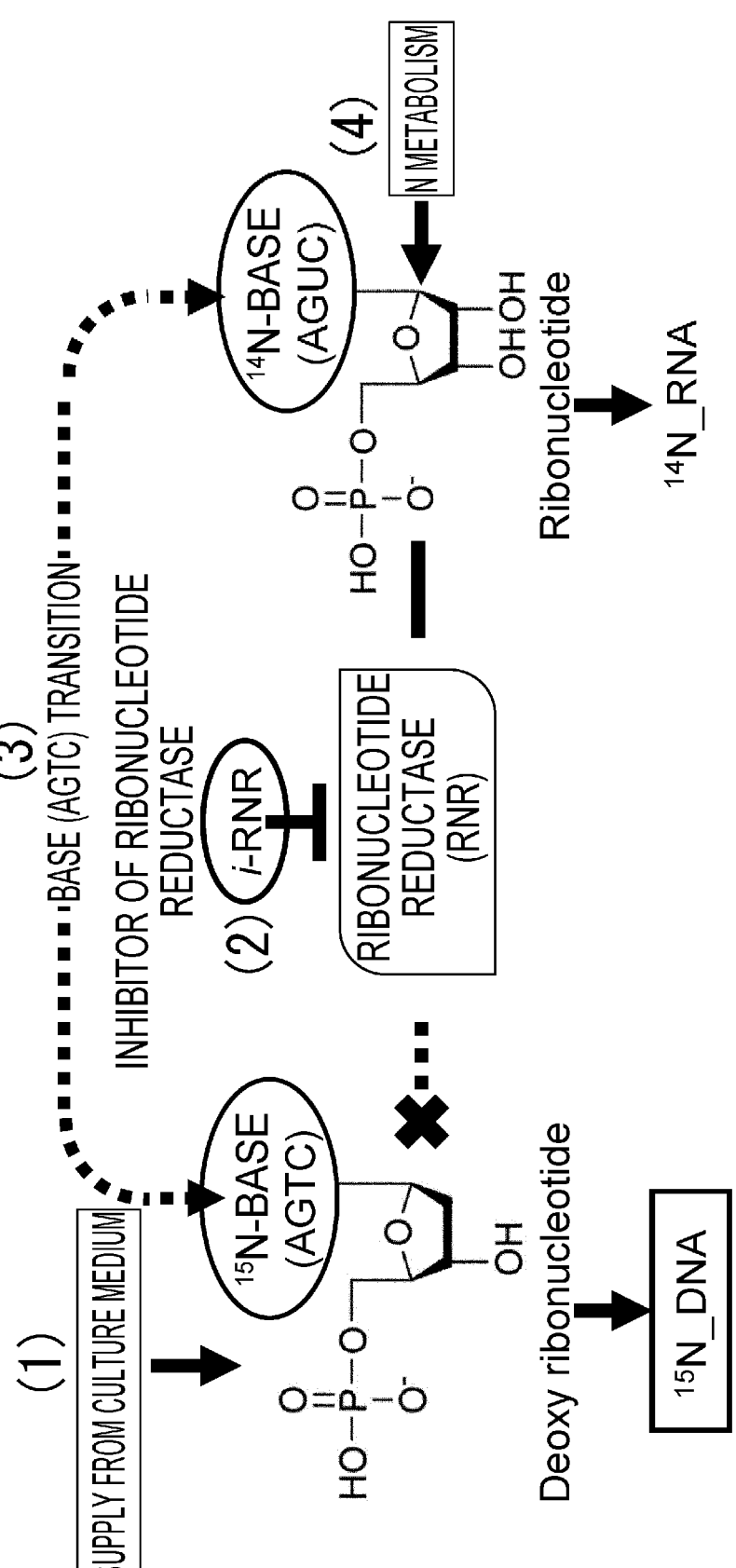
FIG. 10 is a diagram that explains a process of the $^{15}$N-labeling of only DNA in nucleic acid synthesis pathways.

The process of the $^{15}$N-labeling of only DNA in the nucleic acid synthesis pathways in the cell is shown in further detail in FIG. 10. In order to synthesize $^{15}$N-labeled DNA, (1) cell culture is first carried out with $^{15}$N-labeled deoxynucleotides for each of the four bases having been added to the culture medium. Then, since deoxyribonucleotides for DNA synthesis are synthesized only from ribonucleotides by ribonucleotide reductase (RNR), (2) an inhibitor of RNR (i-RNR) is introduced, and conditions are formed in which there is no synthesis in the cell of deoxyribonucleotides not labeled with $^{15}$N. In addition, within the cell, (3) base transition occurs between deoxyribonucleotides and ribonucleotides, and the $^{15}$N-labeled deoxyribonucleotide bases are introduced from outside the cell transition to ribonucleotide bases within the cell, and $^{15}$N_RNA can be directly synthesized. Conversely, the $^{15}$N-unlabeled ribonucleotide bases also transition to deoxyribonucleotide bases. However, (4) the amount of $^{14}$N_ribonucleotide metabolized from, e.g., $^{14}$N_amino acids, in the cell reaches high levels due to the inhibition of RNR according to (2), and the amount of base transition from $^{15}$N_deoxyribonucleotide to ribonucleotide can be inhibited. When, in (1), $^{15}$N_deoxyribonucleotide is introduced into the culture medium in excess, exceeding the amount required for $^{15}$N_DNA synthesis, this can create the likelihood in (3) that $^{15}$N_base transitions from deoxyribonucleotide to ribonucleotide. Accordingly, the amount of $^{15}$N_deoxyribonucleotide introduction into the culture medium can be adjusted as appropriate so as to provide a high $^{15}$N_DNA synthesis efficiency and restrain $^{15}$N_RNA synthesis.

FIG. 11 shows a novel method for carrying out $^{15}$N-labeling of only a target gene or the neighborhood thereof. The base sequence of the $^{15}$N-labeled OR_DNA shown in FIG. 4 is a portion of a gene from the lambda ($\lambda$) phage virus, which infects an *E. coli* host, and is a regulatory gene for suppressing its own growth in order for the $\lambda$ phage to infect the *E. coli* host without killing the host. The $^{15}$N-labeled OR_DNA has three Cro protein binding sites, and the regulatory gene is activated when the Cro protein binds to any one of the sites. The frequency of regulatory gene activation is regulated when, among the three binding sites, a location is introduced where the gene sequence has been mutated. FIG. 4 describes a method for producing $^{15}$N-labeled OR_DNA by a polymerase chain reaction technique. In contrast to this, by synthesizing the 84-base pair OR_DNA without $^{15}$N-labeling and then introducing this into the culture medium, when $^{15}$N-labeled Cro protein is introduced to the *E. coli* that has taken up the regulatory gene, the $^{15}$N-labeled Cro protein binds to the regulatory gene in the *E. coli*. When proton beam irradiation is carried out in this state, the $^{15}$N ($^{1}$H, $\alpha_1\gamma$)$^{12}$C resonant nuclear reaction occurs in the vicinity of the prescribed gene where the $^{15}$N-labeled Cro protein is bound. This method enables mutation to be induced in a prescribed gene at high probabilities.

Example 1: Results of Proton Beam Irradiation of a $^{15}$N-Labeled OR_DNA Sample (1) Preparation of $^{15}$N-Labeled OR_DNA Sample
[Phosphorylation of OR_Primer_R]

The phosphorylation process in support of the evaluation of DNA cleavage after proton beam irradiation is described as follows. ATP (10 mM=mmol/L): 16 μL, OR_primer_R (100 μM): 10 μL, 10×-diluted buffer solution: 16 μL, T4PNK: 8 μL, and sterile water: 110 μL were reacted for 35 minutes at 37° C.; the reaction was then stopped by heating to 72° C., and protein and lipids were removed by PCI extraction (phenol:chloroform:isoamyl alcohol (25:24:1) extraction); and this was followed by ethanol fixation and extraction.

[Synthesis of $^{15}$N-Labeled OR_DNA by PCR Method]

Two types, with and without phosphorylated primer, were synthesized. 35 PCR cycles (98° C.-10 minutes, 31° C.-20 minutes, 72° C.-30 minutes) and finishing were carried out with each of: heat-resistant DNA polymerase (PrimeSTAR® DNA polymerase, commercially available from Takara Bio Inc., Shiga, Japan): 0.5 μL, 5×-diluted buffer solution: 10 μL, $^{15}$N-labeled ($^{15}$N purity ≥98%) dNTP: 6 μL, OR_primer_F (10 μM): 2.5 μL, OR_primer_RP (phosphorylated primer 10 μM): 7.5 μL, template: 1 μL, sterile water: 22.5 μL, heat-resistant DNA polymerase (PrimeSTAR® DNA polymerase, commercially available from Takara Bio Inc., Shiga, Japan): 0.5 μL, 5×-diluted buffer solution: 10 μL, $^{15}$N-labeled ($^{15}$N purity ≥98%) dNTP: 6 μL, OR_primer_F (10 μM): 2.5 μL, OR_primer_R (unphosphorylated primer 10 μM): 2.5 μL, template: 1 μL, sterile water: 27.5 μL. The synthesis of an 84 base pair DNA was confirmed by electrophoresis.

(2) Proton Beam Irradiation

Irradiation samples were prepared by dripping the $^{15}$N-labeled OR_DNA sample or $^{15}$N-unlabeled OR_DNA sample on an Au substrate. The OR_DNA solution concentration was 31.2 ng/μL, and the dripped sample provided by dripping an amount of 13 μL over a dripping area of 0.23 cm$^2$ contained 4.7×10$^{12}$ DNA with at least 538 $^{15}$N atoms being bonded in each DNA. It was 1.1×10$^{16}$ cm$^{-2}$ converted to per the sample area. Proton beam irradiation was carried out using the 4 MV Pelletron® (electrostatic accelerator, commercially available from National Electrostatics Corp., Middleton, Wisconsin, USA) electrostatic accelerator at the National Institute of Advanced Industrial Science and Technology, Tsukuba Center, and the 1 MV tandem electrostatic accelerator at the Research Facility Center for Science and Technology of Tsukuba University. The beam current was 0.1 nA to 5 nA, and the beam irradiation area was 0.071 cm$^2$. The 4.43 MeV gamma-rays emitted by the $^{15}$N ($^1$H, $\alpha_1\gamma$)$^{12}$C resonant nuclear reaction were detected by placing, outside the vacuum at a distance of 24 mm from the irradiation sample, a BGO detector (Bi$_4$Ge$_3$O$_{12}$ crystal scintillator, specific gravity 7.3 gcm$^{-3}$, diameter 76.2 mm×length 79.2 mm), which contains $^{83}$Bi and has the highest detection efficiency for high-energy gamma-rays. The detectable solid angle of the detector is 10% of the omnidirectional angle. When the detection sensitivity for 4.43 MeV gamma-rays is a maximum of 0.1, the detection efficiency for 4.43 MeV gamma-rays is a maximum of about 1%. When the $^{15}$N-labeled OR_DNA sample was irradiated with a proton beam at constant energy, the 4.43 MeV gamma-ray count was 4,000 counts, and the total count for irradiation at 8 points over the energy of 8 keV was 25,000 counts. Considering the detection efficiency, mutation by the $^{15}$N resonant nuclear reaction was produced in at least 2.5×10$^6$ $^{15}$N-labeled OR_DNA.

(3) Ligation of $^{15}$N-Labeled OR_DNA into Linear Plasmid Vector:

[Preparation of A Protruding Ends in $^{15}$N-Labeled OR_DNA]

Four types of mixed solutions were prepared and reacted for 1 hour at 72° C.: proton beam-irradiated $^{15}$N-labeled OR_DNA (9 ng/μL): 6.9 μL, buffer solution (Ex taq) 1 μL, Ex taq 0.1 μL, dATP (10 mM) 2 μL, OR_DNA unirradiated sample (8 ng/μL): 6.9 μL, 10×-diluted buffer solution (Ex taq) 1 μL, Ex taq 0.1 μL, dATP (10 mM) 2 μL, negative insert DNA sample: 6.9 μL, 10×-diluted buffer solution (Ex_taq) 1 μL, Ex_taq 0.1 μL, dATP (10 mM) 2 μL, control insert CI sample (10 ng/μL): 6.9 μL, 10×-diluted buffer solution (Ex_taq) 1 μL, Ex_taq 0.1 μL, dATP (10 mM) 2 μL.

[Ligation with Linear Plasmid Vector]

The aforementioned four types of mixed solutions were mixed with a linear plasmid vector (T-Vector pMD19, 2, 692 base pairs) on ice and, after standing for 30 minutes, a 30-second thermal shock at 42° C. was applied to increase the transformation efficiency.

[Culture of Ampicillin-Resistant E. coli]

E. coli (JM109) that had been shaking-cultured on M9 culture medium at 180 rpm and a temperature of 37° C. was seeded to ampicillin-containing culture media into which the four types of cyclic plasmid vectors had been introduced, and colony formation by the JM109 was compared. 46 colonies/11 ng DNA was obtained for the culture medium that contained the cyclic plasmid vector ligated with the non-beam-irradiated sample, while a reduction to less one-third, or 13 colonies/11 ng DNA, was obtained for the culture medium that contained the cyclic plasmid vector ligated with beam-irradiated $^{15}$N-labeled OR_DNA.

Example 2: Results of Proton Beam Irradiation of E. coli Biological Samples

Since proton beam irradiation is carried out substantially in a vacuum, the E. coli (JM109) was first converted into a freeze-dried state, and its durability was investigated. 10 μL of E. coli JM109 solution was introduced into an Eppendorf tube and was divided into a sample temporarily frozen at the temperature of liquid nitrogen and a sample not frozen by liquid nitrogen. Each was introduced into a vacuum dryer at −20° C. and held for 4 hours and then removed and held for an additional 24 hours at 4° C. to produce freeze-dried samples. The survival rate of the E. coli JM109 at this point was 26.8% for the sample frozen with liquid nitrogen and 39.1% for the sample not frozen with liquid nitrogen.

E. coli JM109 has 514 million base pairs of DNA, and $^{15}$N-labeling of this DNA was carried out by two methods. In one method, E. coli JM109 is cultured, without the introduction of the glutamine synthetase inhibitor MSX, on a culture medium containing $^{15}$N-labeled ammonium ion, and all the nitrogen within the cell, including proteins and nucleic acids, is labeled with $^{15}$N (sample F). In the other method, E. coli JM109 is cultured, with the introduction of MSX and $^{15}$N-unlabeled glutamine, on a culture medium containing $^{15}$N-labeled deoxynucleotides, to yield a biological sample in which only the DNA and RNA is $^{15}$N-labeled (sample D).

Proton beam irradiation samples were produced by preparing three solutions from the two types of $^{15}$N-labeled E. coli JM109 and from $^{15}$N-unlabeled E. coli JM109 (sample E). The E. coli concentration, dripped amount of solution, dripped area, number of dripped cells, the area density of cells, and $^{15}$N area density for each irradiation sample are as follows.

[Sample D]

E. coli concentration: 3.17×10$^8$ cells/mL, dripped amount of solution: 10 μL, dripped area: 1.26 cm$^2$, number of dripped cells: 3.17×10$^6$ cells, area density of cells: 2.52×10$^6$ cells/cm$^2$, and $^{15}$N area density: 9.50×10$^{13}$ cm$^{-2}$.

[Sample E]

E. coli concentration: 3.17×10$^8$ cells/mL, dripped amount of solution: 10 μL, dripped area: 1.20 cm$^2$, number of dripped cells: 3.17×10$^6$ cells, area density of cells: 2.64× 10$^6$ cells/cm$^2$, and $^{15}$N area density: 3.66×10$^{11}$ cm$^{-2}$.

[Sample F]

E. coli concentration: 8.62×10$^7$ cells/mL, dripped amount of solution: 20 μL, dripped area: 1.56 cm$^2$, number of dripped cells: 1.72×10$^6$ cells, area density of cells: 1.11×10$^6$ cells/cm$^2$, and $^{15}$N area density: 4.18×10$^{13}$ cm$^{-2}$.

The amount of 4.43 MeV γ-radiation counted at the same time as proton beam irradiation showed that the ratio of the amount of $^{15}$N for the $^{15}$N-labelling of only DNA and RNA in sample D was 1 to 44.6 for the case in which the nitrogen in the entire cell in sample F was labeled with $^{15}$N.

Figure 12:
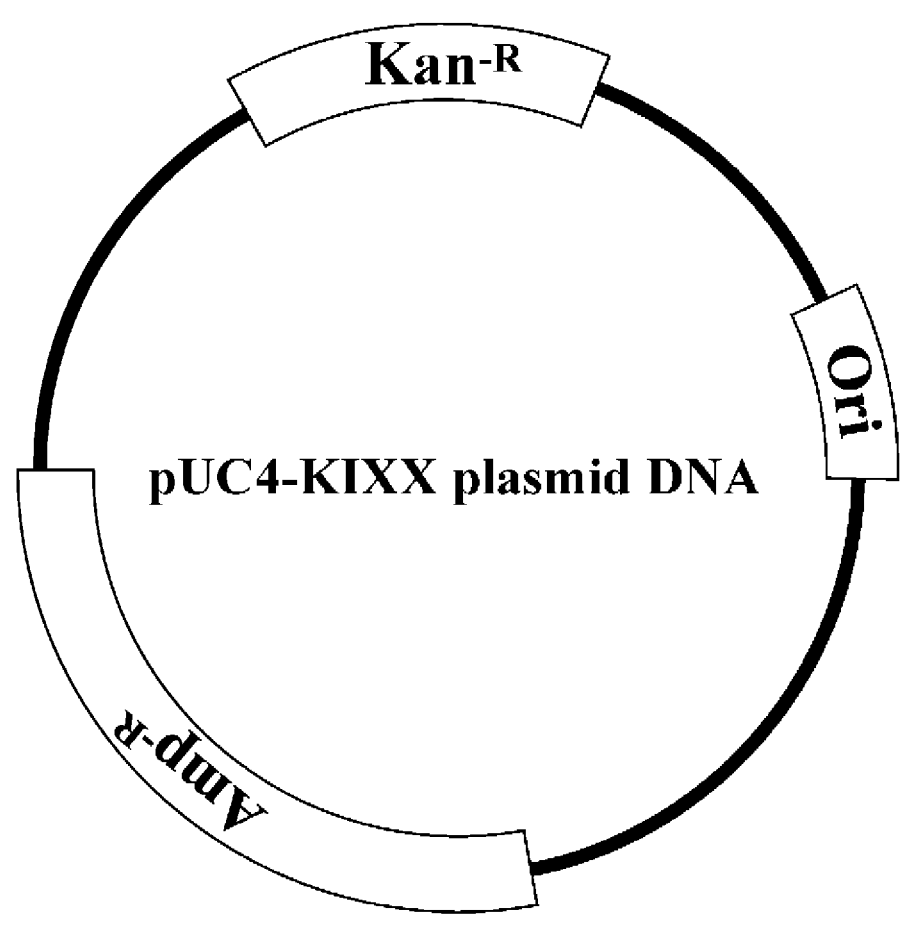
FIG. 12 is a diagram that shows the gene structure of the pUC4-KIXX cyclic plasmid.

Example 3: Results of Proton Beam Irradiation of $^{15}$N-Labeled Drug-Resistance Gene Plasmid Samples (1) pUC4-KIXX Plasmid and Method for Producing Same The gene structure of the pUC4-KIXX plasmid (plasmid DNA) is shown in FIG. 12. This plasmid is a cyclic plasmid (3,853 base pairs (bps)) provided by the insertion of a kanamycin-resistance gene (Kanamycin-R, 1,248 bps) into the pUC4 gene (2,605 bps), which has Ori and an ampicillin-resistance gene (Ampicillin-R). The gene size taken up by the promoter and transcription region for the two drug-resistance genes is 934 bps for the ampicillin-resistance gene and 953 bps for the kanamycin-resistance gene, and the Ori region required for plasmid replication is 621 bps. The base pair types and number of $^{15}$N (100% substitution) for each gene region are given in Table 2.

16 the 1 MV tandem electrostatic accelerator at the Research Facility Center for Science and Technology of Tsukuba University. The proton beam irradiation conditions were the same as in (2) of Example 2. The resonance curve for the $^{15}$N ($^1$H, $\alpha_1\gamma$)$^{12}$C resonant nuclear reaction of the $^{15}$N_pUC4-KIXX plasmid sample is given in FIG. 13. The resonance curve acquired for the $^{15}$N-labeled deoxyribonucleotide $^{15}$N-labeled dGTP is also shown for reference. Proton beam irradiation was carried out by dividing the proton energy into three beam levels in 4 keV steps between 890 keV and 906 keV. The three irradiation levels are given in Table 3.

TABLE 3

| Sample | Energy (KeV) | Irradiation time (s) | Irradiation dose (µC) | Total irradiation dose (µC) |
|---|---|---|---|---|
| ① 15N_pUC4-KIXX | 890 | 435 | 0.5005 | 2.5524 |
| | 894 | 434 | 0.5004 | |
| | 898 | 437 | 0.5005 | |

TABLE 2

| | 15N labeled pUC4-KIXX plasmid DNA | | | | | | | | | |
|---|---|---|---|---|---|---|---|---|---|---|
| Base pairs | Ampicillin-R (bps)* | 15N | Ori (bps) | 15N | Kanamycin-R (bps)* | 15N | Other area (bps) | 15N | Total (bps) | 15N |
| A-T | 233 | 1631 | 136 | 952 | 263 | 1841 | 366 | 2562 | 998 | 6986 |
| T-A | 254 | 1778 | 148 | 1036 | 289 | 2023 | 307 | 2149 | 998 | 6986 |
| C-G | 233 | 1864 | 177 | 1416 | 189 | 1512 | 312 | 2496 | 911 | 7288 |
| G-C | 214 | 1712 | 160 | 1280 | 212 | 1696 | 360 | 2880 | 946 | 7568 |
| Total | 934 | 6985 | 621 | 4684 | 953 | 7072 | 1345 | 10087 | 3853 | 28828 |

*Promoter + coding area

A plasmid containing $^{15}$N at its natural abundance and a plasmid containing ≥98% $^{15}$N were produced using the following method. 250 mL of M9 minimal medium in which the nitrogen source was NH$_4$Cl containing $^{15}$N at its natural abundance (0.364%) was prepared. 250 mL of M9 minimal medium in which the nitrogen source was $^{15}$NH$_4$Cl containing ≥98% $^{15}$N was also prepared. Specifically, each of these M9 minimal media was prepared by dissolving Na$_2$HPO$_4$ (15 g), KH$_2$PO$_4$ (7.5 g), NaCl (1.25 g), NH$_4$Cl (2.5 g), 1 M (mol/L) MgSO$_4$ (250 µL), 20% (w/v) glucose 2.5 mL, and 1 M CaCl$_2$ (25 µL) in 250 mL of ultrapure water, followed by autoclaving and then cooling to room temperature and then the addition of 250 µL of 1% thiamine-HCl. E. coli (JM109) holding the pUC4-KIXX plasmid was cultured on each of these culture media. Specifically, 25 UL of the E. coli was added to the M9 minimal medium, and shake culture was carried out for 2 days at 37° C. and 200 rpm. The E. coli was then recovered, and plasmid purification was carried out using a Plasmid Midi kit (Qiagen) plasmid extraction kit. The plasmids were dissolved in sterile water, and the DNA concentration was quantitated with a NanoDrop® (fluorometer commercially available from, Thermo Fisher Scientific Inc. Waltham, Massachusetts, USA) fluorometer and adjusted to a concentration of 115 ng/µL. $^{14}$N_pUC4_KIXX, a plasmid containing $^{15}$N in its natural abundance, and $^{15}$N_pUC4-KIXX, a plasmid containing $^{15}$N at ≥98%, were produced using this procedure.

(2) Proton Beam Irradiation of pUC4-KIXX Plasmids

For each of the two plasmid samples, 1 µL was dripped onto an Si wafer substrate followed by drying, placement in the vacuum chamber, and irradiation of the sample with a proton beam. Proton beam irradiation was carried out using TABLE 3-continued

| Sample | Energy (KeV) | Irradiation time (s) | Irradiation dose (µC) | Total irradiation dose (µC) |
|---|---|---|---|---|
| | 902 | 441 | 0.5005 | |
| | 906 | 488 | 0.5505 | |
| ② 15N_pUC4-KIXX | 890 | 889 | 1.0006 | 5.0533 |
| | 894 | 879 | 1.0504 | |
| | 898 | 828 | 1.0009 | |
| | 902 | 835 | 1.0005 | |
| | 906 | 860 | 1.0009 | |
| ③ 15N_pUC4-KIXX | 890 | 1658 | 2.0002 | 10.001 |
| | 894 | 1541 | 2.0003 | |
| | 898 | 1477 | 2.0003 | |
| | 902 | 1857 | 2.0001 | |
| | 906 | 1939 | 2.0001 | |
| ④ 14N_pUC4-KIXX | 890 | 438 | 0.5003 | 2.5015 |
| | 894 | 441 | 0.5001 | |
| | 898 | 454 | 0.5004 | |
| | 902 | 458 | 0.5002 | |
| | 906 | 467 | 0.5005 | |
| ⑤ 14N_pUC4-KIXX | 890 | 850 | 1.0005 | 5.0028 |
| | 894 | 820 | 1.0004 | |
| | 898 | 799 | 1.0005 | |
| | 902 | 803 | 1.0005 | |
| | 906 | 822 | 1.0009 | |
| ⑥ 14N_pUC4-KIXX | 890 | 1904 | 2.0003 | 10.0012 |
| | 894 | 1799 | 1.9999 | |
| | 898 | 1733 | 2.0003 | |
| | 902 | 1739 | 2.0005 | |
| | 906 | 1834 | 2.0002 | |

(3) Transformation with Proton Beam-Irradiated Plasmids 8.6 ng of the proton beam-irradiated plasmid was added to 50 µL of E. coli (1×10$^{10}$ cells/mL), and the plasmid was introduced into the E. coli cells by electroporation. The electroporation process was run for a current passage interval of 3.5 to 3.7 ms using a direct-current field, a voltage of 1,500 V, a resistance of 200Ω, and a capacitance of 25 μF. 1 mL of LB medium was added and shaking culture was carried out for 1 hour (37° C., 200 rpm). During this culturing process, the plasmids, that were damaged by proton beam irradiation with cleavage of the circular form to be a linear shape, were not replicated in the *E. coli* cells, and as a consequence, of the proton beam-irradiated plasmids, only the plasmids that retained the circular form were amplified with the occurrence of transformation.

(4) Evaluation of the Degree of Damage to Drug-Resistance Genes

Figure 14:
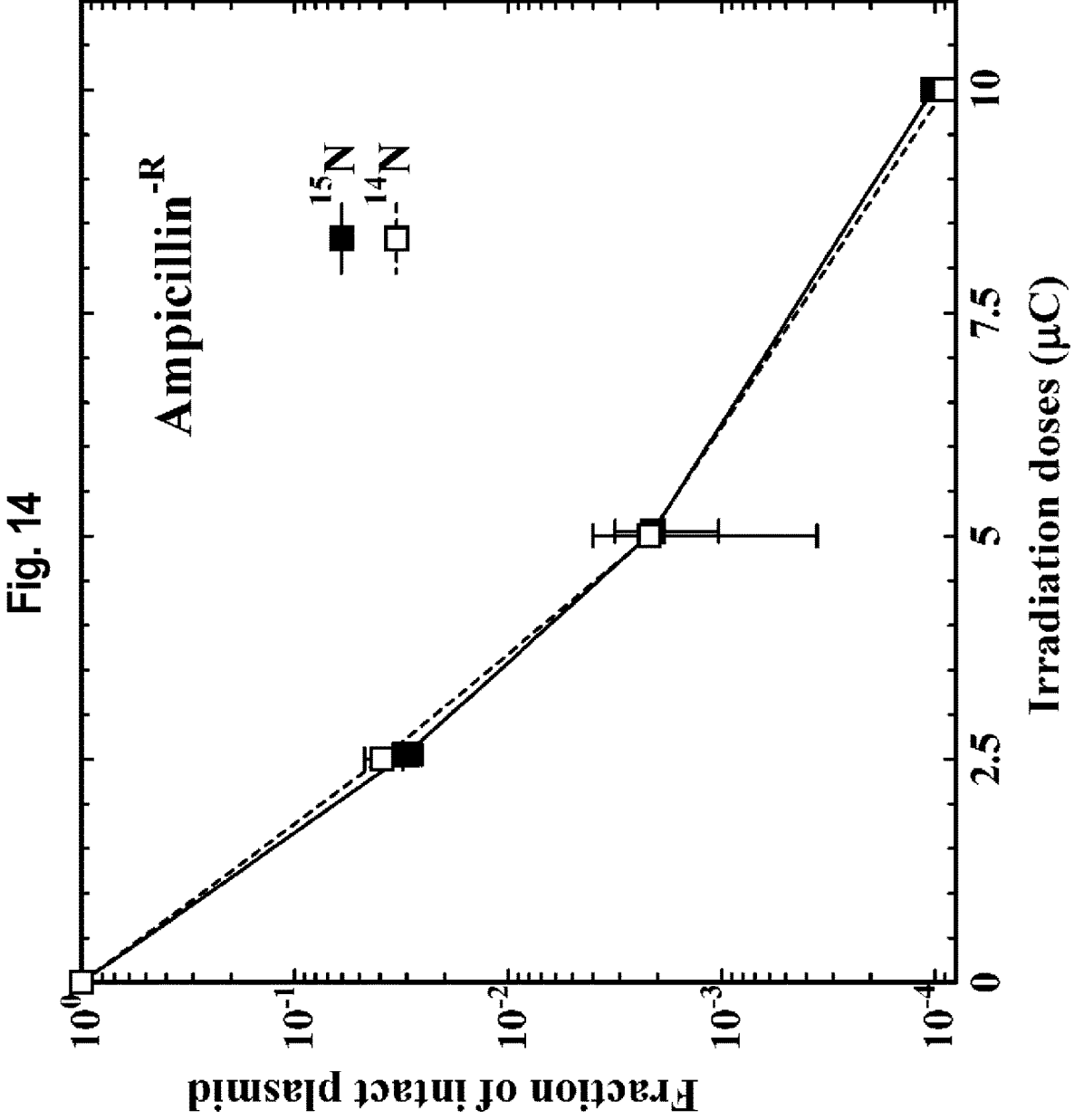
FIG. 14 is a graph that shows the relationship between gene damage and the amount of proton beam irradiation of a plasmid. The proton beam-irradiated plasmid was introduced into *Escherichia coli*, and the *E. coli* was cultured on a culture medium to which ampicillin had been added.
Figure 15:
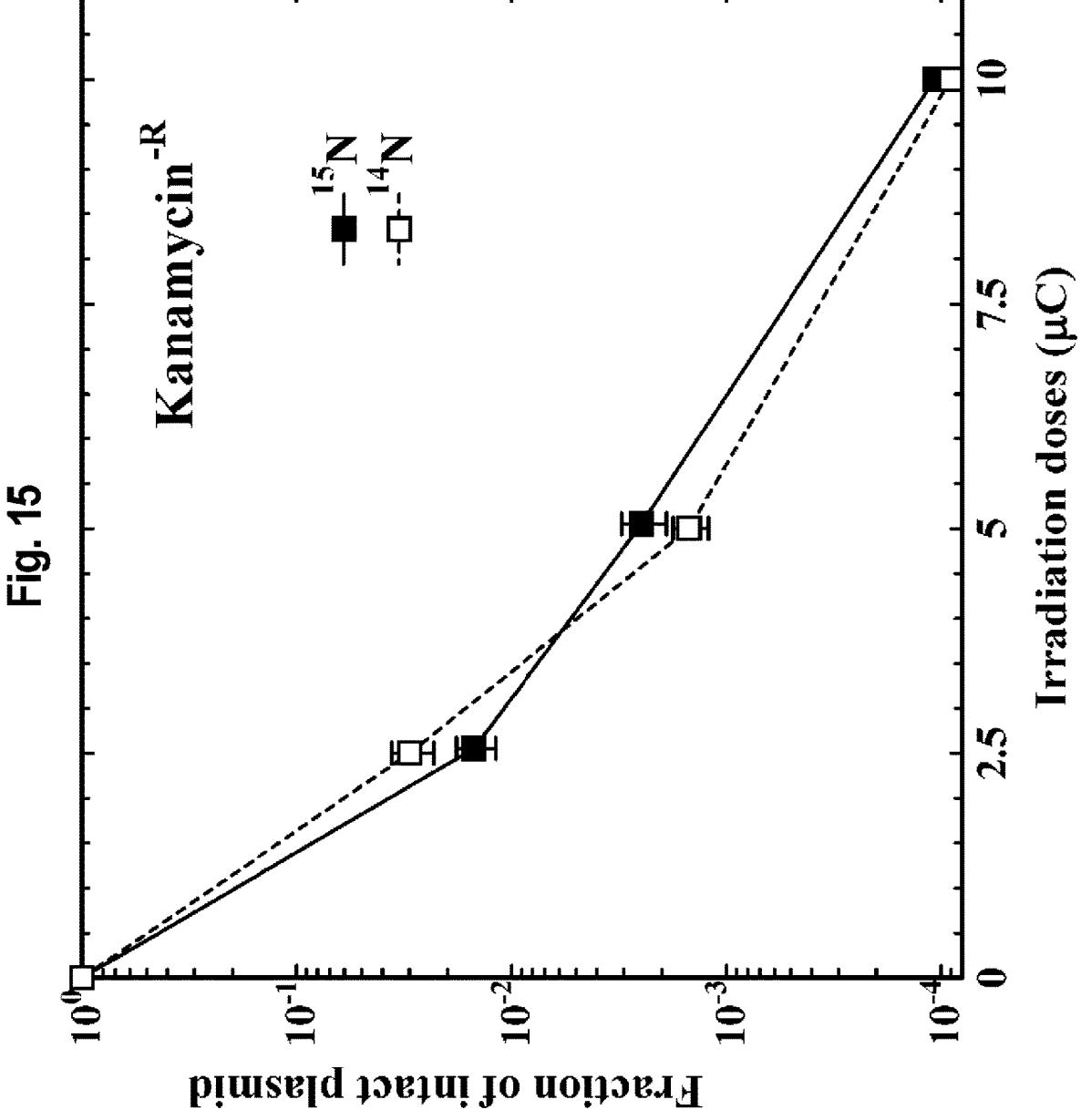
FIG. 15 is a graph that shows the relationship between gene damage and the amount of proton beam irradiation of a plasmid. The proton beam-irradiated plasmid was introduced into *E. coli* and the *E. coli* was cultured on a culture medium to which kanamycin had been added.
Figure 16:
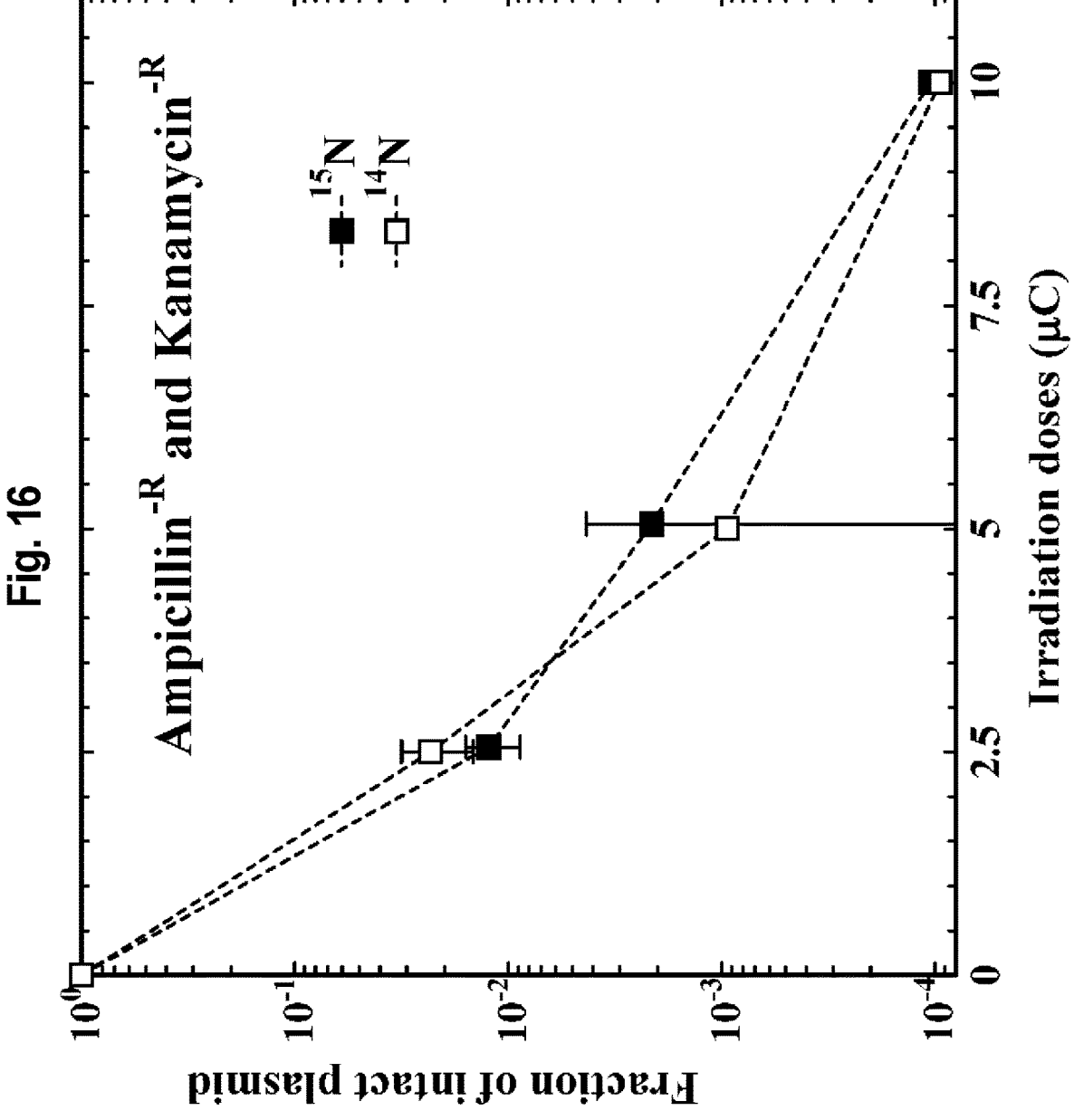
FIG. 16 is a graph that shows the relationship between gene damage and the amount of proton beam irradiation of a plasmid. The proton beam-irradiated plasmid was introduced into *E. coli* and the *E. coli* was cultured on a culture medium to which ampicillin and kanamycin had been added.

Three types of culture plates with the addition of the two drugs were prepared. A 100 μL aliquot of *E. coli* transformed with proton beam-irradiated plasmid was seeded to each of the following culture plates and the number of colonies formed was analyzed: (a) 100 μg/mL ampicillin, (b) 50 μg/mL kanamycin, (c) 100 μg/mL ampicillin+50 μg/mL kanamycin. As a control sample, a 100 μL aliquot with the unirradiated plasmid was also seeded to the three culture plates to which the drugs had been introduced in the same manner. The numbers of colonies appearing on the three drug-added culture plates are given in FIG. 14, FIG. 15, and FIG. 16. The vertical axis shows values normalized by the number of colonies appearing for the control sample (=1.0), and the average value for three measurements is given. The upper limit and lower limit on the results of the three measurements are given for the error. The colony generation count at 10 μC was 0 in each figure, but the value of the detection limit is plotted in the figures. The vertical axis shows the fraction that functions normally in the absence of damage to the two drug-resistance genes in the plasmid by proton beam irradiation. At a total irradiation dose of 2.5 μC, it is shown that the $^{15}N\_pUC4$-KIXX plasmid receives greater irradiation damage in excess of the error. This result shows that the $^{15}N$ ($^{1}H$, $\alpha_1\gamma$)$^{12}C$ resonant nuclear reaction imparts substantial damage to genes in excess of the ionization effects of the proton beam. It is considered that the genes receive nonspecific damage when the total irradiation dose in FIG. 14 reaches about 5.0 μC or higher.

The embodiments described in the preceding have the purpose of facilitating an understanding of the present invention and are not intended to limit the interpretation of the present invention. The individual elements provided in the embodiments, as well as their positions, materials, conditions, shapes, sizes, and so forth, should not be construed as being limited to that which has been provided as exemplary and may be modified as appropriate. In addition, the structures shown in different embodiments may be partially replaced by or combined with each other.

---

What is claimed is:

1. A method for mutating a gene comprising:
labeling a DNA with $^{15}N$; and
irradiating the DNA with a proton beam having energy at which $^{15}N$ undergoes a resonant nuclear reaction,
wherein the labeling of the DNA with $^{15}N$ comprises replacing N in the DNA with $^{15}N$.

2. The method, according to claim 1, further comprising changing energy that produces the resonant nuclear reaction of $^{15}N$.

3. The method, according to claim 1, further comprising detecting the resonant nuclear reaction.

4. The method, according to claim 3, wherein an amount of 4.43 MeV gamma-ray is counted in the detection.

5. A method for mutating a gene comprising:
labeling a DNA with $^{15}N$; and
irradiating the DNA with a proton beam having energy at which $^{15}N$ undergoes a resonant nuclear reaction,
wherein the labeling of the DNA with $^{15}N$ comprises binding a $^{15}N$-labeled biomolecule to the DNA.

6. The method according to claim 5, wherein the biomolecule is a protein.

7. A method for mutating a gene comprising:
labeling a DNA with $^{15}N$; and
irradiating the DNA with a proton beam having energy at which $^{15}N$ undergoes a resonant nuclear reaction,
wherein the DNA in a living cell is labeled with $^{15}N$, and
wherein $^{15}N$ is maintained at the natural abundance in non-DNA cellular components in the living cell, and the $^{15}N$ abundance in the DNA is larger than the natural abundance.

8. A method for mutating a gene comprising:
labeling a DNA with $^{15}N$; and
irradiating the DNA with a proton beam having energy at which $^{15}N$ undergoes a resonant nuclear reaction, wherein the DNA in a living cell is labeled with $^{15}N$, and
wherein the labeling of the DNA with $^{15}N$ in the living cell comprises introducing into the living cell a $^{15}N$-labeled deoxyribonucleotide and an inhibitor of glutamine synthetase.

9. The method, according to claim 8, wherein the labeling of the DNA with $^{15}N$ in the living cell further comprises introducing $^{15}N$-unlabeled glutamine into the living cell.

10. A method for mutating a gene comprising:
labeling a DNA with $^{15}N$; and
irradiating the DNA with a proton beam having energy at which $^{15}N$ undergoes a resonant nuclear reaction,
wherein the DNA in a living cell is labeled with $^{15}N$, and
wherein the labeling of the DNA with $^{15}N$ in the living cell comprises introducing into the living cell a $^{15}N$-labeled deoxyribonucleotide and an inhibitor of ribonucleotide reductase.

11. The method, according to claim 10, wherein the labeling of the DNA with $^{15}N$ in the living cell further comprises introducing $^{15}N$-unlabeled glutamine into the living cell.

12. A method for mutating a gene comprising:
labeling a DNA with $^{15}N$;
irradiating the DNA with a proton beam having energy at which $^{15}N$ undergoes a resonant nuclear reaction; and
detecting the resonant nuclear reaction,
wherein an amount of 4.43 MeV gamma-ray is counted in the detection, and
wherein the method further comprises calculating, based on the amount of gamma-ray counted, the number of mutations produced in the DNA.

13. The method according to claim 12, wherein the amount of gamma-ray produced by a resonant nuclear reaction that occurs in a reference sample in which the number of $^{15}N$ atoms is known is referred in the calculation.

* * * * *

SEQUENCE LISTING

```
<160> NUMBER OF SEQ ID NOS: 21

<210> SEQ ID NO 1
<211> LENGTH: 84
<212> TYPE: DNA
<213> ORGANISM: Artificial Sequence
<220> FEATURE:
<223> OTHER INFORMATION: Description of Artificial Sequence: Synthetic
      OR_WT_F sequence

<400> SEQUENCE: 1
tacgttaaat ctatcaccgc aagggataaa tatctaacac cgtgcgtgtt gactatttta        60
cctctggcgg tgataatggt tgca                                              84

<210> SEQ ID NO 2
<211> LENGTH: 84
<212> TYPE: DNA
<213> ORGANISM: Artificial Sequence
<220> FEATURE:
<223> OTHER INFORMATION: Description of Artificial Sequence: Synthetic
      OR_WT_R sequence

<400> SEQUENCE: 2
tgcaaccatt atcaccgcca gaggtaaaat agtcaacacg cacggtgtta gatatttatc        60
ccttgcggtg atagatttaa cgta                                              84

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic
      OR_primer_F sequence

<400> SEQUENCE: 3
tacgttaaat c                                                            11

<210> SEQ ID NO 4
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tacgttaaat ctatcaccgc aag                                                23

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tggcggtgat aatggttgca                                                    20

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cttgcggtga tagatttaac gta                                                23

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tgcaaccatt atcaccgcca                                                    20

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tacgttaaat ctatcaccgc aag                                                23

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tggcggtgat aatggttgca                                                    20

<210> SEQ ID NO 10
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cttgcggtga tagatttaac gta                                                     23

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tgcaaccatt atcaccgcca                                                         20

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tacgttaaat ctatcaccgc aag                                                     23

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tggcggtgat aatggttgca                                                         20

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cttgcggtga tagatttaac gta                                                     23

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tgcaaccatt atcaccgcca                                                         20

<210> SEQ ID NO 16
<211> LENGTH: 18
<212> TYPE: DNA
```

-continued

<213> ORGANISM: Artificial Sequence
<220> FEATURE:
<223> OTHER INFORMATION: Description of Artificial Sequence: Synthetic
      oligonucleotide

<400> SEQUENCE: 16
ggtgatagat ttaacgta                                                    18

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tggcggtgat aatggttgca                                                  20

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tacgttaaat ctatcaccgc aag                                              23

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tgcaaccatt atcaccgcca                                                  20

<210> SEQ ID NO 20
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tacgttaaat ctatcaccgc aagggataaa tatctaaggt agtgtacttt gactatttta      60
cggtaggcta ctataatggt tgca                                             84

<210> SEQ ID NO 21
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tgcaaccatt atagtagcct accgtaaaat agtcaaagta cactacctta gatatttatc      60
ccttgcggtg atagatttaa cgta                                             84